(12) United States Patent
Thenuwara et al.

(10) Patent No.: US 8,753,352 B2
(45) Date of Patent: *Jun. 17, 2014

(54) TOOLS, SYSTEMS, AND METHODS FOR INSERTING A PRE-CURVED ELECTRODE ARRAY PORTION OF A LEAD INTO A BODILY ORIFICE

(75) Inventors: Chuladatta Thenuwara, Castaic, CA (US); Timothy Beerling, Los Angeles, CA (US); Mark Downing, Valencia, CA (US); Paul Hoffman, Valencia, CA (US); William G. Orinski, Reno, NV (US)

(73) Assignee: Advanced Bionics AG, Zug (CH)

( * ) Notice: Subject to any disclaimer, the term of this patent is extended or adjusted under 35 U.S.C. 154(b) by 822 days.

This patent is subject to a terminal disclaimer.

(21) Appl. No.: 12/824,119

(22) Filed: Jun. 25, 2010

(65) Prior Publication Data
US 2011/0319908 A1 Dec. 29, 2011

(51) Int. Cl.
*A61B 19/00* (2006.01)
(52) U.S. Cl.
USPC ............................................. 606/129
(58) Field of Classification Search
USPC .................. 606/129; 607/56, 116, 136, 137; 600/379
See application file for complete search history.

(56) References Cited

U.S. PATENT DOCUMENTS

| | | | |
|---|---|---|---|
| 3,530,860 A | 9/1970 | Majoros | |
| 3,973,560 A | 8/1976 | Emmett | |
| 4,180,080 A | 12/1979 | Murphy | |
| 4,280,510 A | 7/1981 | O'Neill | |
| 4,488,561 A | 12/1984 | Doring | |
| 4,532,930 A | 8/1985 | Crosby et al. | |
| 4,646,755 A | 3/1987 | Kane | |
| 4,665,918 A | 5/1987 | Garza et al. | |

(Continued)

FOREIGN PATENT DOCUMENTS

| EP | 0109304 | 5/1984 |
|---|---|---|
| EP | 0328597 | 8/1989 |

(Continued)

OTHER PUBLICATIONS

International Search Report and Written Opinion received in International Application No. PCT/US2011/041577, dated Nov. 30, 2011.

(Continued)

*Primary Examiner* — Katherine Dowe
*Assistant Examiner* — Erin Colello
(74) *Attorney, Agent, or Firm* — ALG Intellectual Property, LLC

(57) ABSTRACT

Exemplary insertion tools, systems, and methods for inserting a pre-curved electrode array portion of a lead into a bodily orifice are described herein. An exemplary insertion tool includes a handle assembly, a slider assembly, an insertion assembly coupled to the handle assembly, and a retractor assembly disposed at least partially within the handle assembly and configured to selectively couple to a straightening member inserted into the pre-curved electrode array portion and at least partially retract the straightening member from the pre-curved electrode array portion in response to actuation by a user of the slider assembly. The retractor assembly may comprise a spring-loaded retractor member configured to move from a distal position to a proximal position in response to actuation by the user of the slider assembly to at least partially retract the straightening member from the pre-curved electrode array portion. Corresponding insertion tools, systems, and methods are also described.

23 Claims, 25 Drawing Sheets

(56) References Cited

U.S. PATENT DOCUMENTS

| | | | |
|---|---|---|---|
| 4,787,884 A | 11/1988 | Goldberg | |
| 4,819,647 A | 4/1989 | Byers et al. | |
| 4,865,037 A | 9/1989 | Chin et al. | |
| 4,898,183 A | 2/1990 | Kuzma | |
| 4,994,069 A | 2/1991 | Ritchart et al. | |
| 5,046,497 A | 9/1991 | Millar | |
| 5,110,529 A | 5/1992 | Arima | |
| 5,159,861 A | 11/1992 | Anderson | |
| 5,312,415 A | 5/1994 | Palermo | |
| 5,314,464 A * | 5/1994 | KenKnight et al. | 607/132 |
| 5,443,493 A | 8/1995 | Byers et al. | |
| 5,545,200 A | 8/1996 | West et al. | |
| 5,545,219 A | 8/1996 | Kuzma | |
| 5,558,673 A | 9/1996 | Edwards et al. | |
| 5,579,780 A * | 12/1996 | Zadini et al. | 600/585 |
| 5,645,585 A | 7/1997 | Kuzma | |
| 5,667,514 A | 9/1997 | Heller | |
| 5,749,371 A * | 5/1998 | Zadini et al. | 600/585 |
| 5,810,852 A | 9/1998 | Greenberg et al. | |
| 5,814,062 A | 9/1998 | Sepetka et al. | |
| 5,902,331 A | 5/1999 | Bonner et al. | |
| 5,906,619 A | 5/1999 | Olson et al. | |
| 5,999,859 A | 12/1999 | Jolly | |
| 6,070,105 A | 5/2000 | Kuzma | |
| 6,071,282 A | 6/2000 | Fleischman | |
| 6,078,841 A * | 6/2000 | Kuzma | 607/137 |
| 6,093,197 A | 7/2000 | Bakula et al. | |
| 6,119,044 A | 9/2000 | Kuzma | |
| 6,125,302 A * | 9/2000 | Kuzma | 607/137 |
| 6,129,753 A | 10/2000 | Kuzma | |
| 6,149,657 A * | 11/2000 | Kuzma | 606/129 |
| 6,163,729 A * | 12/2000 | Kuzma | 607/137 |
| 6,195,586 B1 * | 2/2001 | Kuzma | 607/137 |
| 6,208,882 B1 | 3/2001 | Lenarz et al. | |
| 6,219,580 B1 | 4/2001 | Faltys et al. | |
| 6,272,382 B1 | 8/2001 | Faltys et al. | |
| 6,293,945 B1 * | 9/2001 | Parins et al. | 606/45 |
| 6,304,785 B1 * | 10/2001 | McCreery et al. | 607/116 |
| 6,308,101 B1 | 10/2001 | Faltys et al. | |
| 6,312,429 B1 * | 11/2001 | Burbank et al. | 606/47 |
| 6,321,125 B1 | 11/2001 | Kuzma | |
| 6,421,569 B1 | 7/2002 | Treaba et al. | |
| 6,500,130 B2 | 12/2002 | Kinsella et al. | |
| 6,547,762 B1 * | 4/2003 | Botich et al. | 604/110 |
| 6,582,441 B1 | 6/2003 | He et al. | |
| 6,604,283 B1 | 8/2003 | Kuzma | |
| 6,746,412 B1 | 6/2004 | Hill et al. | |
| 6,858,034 B1 | 2/2005 | Hijlkema et al. | |
| 6,866,669 B2 | 3/2005 | Buzzard | |
| 6,936,065 B2 | 8/2005 | Khan et al. | |
| 6,939,352 B2 | 9/2005 | Buzzard | |
| 6,968,238 B1 * | 11/2005 | Kuzma | 607/137 |
| 7,050,858 B1 * | 5/2006 | Kuzma et al. | 607/137 |
| 7,063,708 B2 | 6/2006 | Gibson et al. | |
| 7,269,461 B2 | 9/2007 | Dadd et al. | |
| 7,349,744 B2 * | 3/2008 | Dadd et al. | 607/137 |
| 7,544,197 B2 | 6/2009 | Kelsch et al. | |
| 7,591,268 B2 | 9/2009 | Lowe et al. | |
| 7,753,887 B2 * | 7/2010 | Botich et al. | 604/164.12 |
| 7,792,586 B2 | 9/2010 | Dadd et al. | |
| 7,966,077 B2 * | 6/2011 | Risi | 607/137 |
| 2002/0045927 A1 * | 4/2002 | Moore et al. | 607/116 |
| 2002/0143302 A1 * | 10/2002 | Hinchliffe et al. | 604/272 |
| 2002/0147484 A1 | 10/2002 | Dahl | |
| 2003/0045921 A1 | 3/2003 | Dadd et al. | |
| 2003/0093139 A1 | 5/2003 | Gibson et al. | |
| 2003/0171758 A1 * | 9/2003 | Gibson et al. | 606/129 |
| 2004/0122312 A1 * | 6/2004 | Chesbrough et al. | 600/431 |
| 2004/0127968 A1 | 7/2004 | Kuzma et al. | |
| 2004/0193203 A1 * | 9/2004 | Pak et al. | 606/187 |
| 2004/0220651 A1 | 11/2004 | Kuzma et al. | |
| 2004/0243177 A1 | 12/2004 | Svehla et al. | |
| 2004/0260371 A1 | 12/2004 | Greenland et al. | |
| 2005/0004644 A1 | 1/2005 | Kelsch et al. | |
| 2005/0075606 A1 | 4/2005 | Botich et al. | |
| 2005/0251237 A1 | 11/2005 | Kuzma et al. | |
| 2006/0058861 A1 * | 3/2006 | Gibson et al. | 607/137 |
| 2006/0155353 A1 | 7/2006 | Heil, Jr. | |
| 2006/0241723 A1 * | 10/2006 | Dadd et al. | 607/57 |
| 2007/0043419 A1 | 2/2007 | Nikolchev et al. | |
| 2007/0111175 A1 * | 5/2007 | Raven et al. | 434/262 |
| 2007/0213812 A1 | 9/2007 | Webler et al. | |
| 2007/0233214 A1 | 10/2007 | Chitre et al. | |
| 2008/0004684 A1 | 1/2008 | Dadd et al. | |
| 2008/0082141 A1 * | 4/2008 | Risi | 607/57 |
| 2008/0109011 A1 | 5/2008 | Thenuwara et al. | |
| 2008/0195146 A1 | 8/2008 | Wardle | |
| 2008/0269740 A1 * | 10/2008 | Bonde et al. | 606/53 |
| 2008/0269763 A1 * | 10/2008 | Bonde et al. | 606/99 |
| 2009/0119920 A1 | 5/2009 | Peschke et al. | |
| 2011/0301681 A1 | 12/2011 | Risi | |

FOREIGN PATENT DOCUMENTS

| | | |
|---|---|---|
| EP | 1233810 | 8/2002 |
| EP | 1341578 | 9/2003 |
| EP | 1370205 | 12/2003 |
| EP | 1370205 B1 * | 12/2003 |
| EP | 1476104 | 11/2004 |
| EP | 2039323 | 3/2009 |
| WO | WO-80/02231 | 10/1980 |
| WO | WO-8900870 | 2/1989 |
| WO | WO-9324058 | 12/1993 |
| WO | WO-95/11710 | 5/1995 |
| WO | WO-9720530 | 6/1997 |
| WO | WO-00/64529 | 11/2000 |
| WO | WO-00/71063 | 11/2000 |
| WO | WO-01/68177 | 9/2001 |
| WO | WO-02/30507 | 4/2002 |
| WO | WO-0230507 | 4/2002 |
| WO | WO-0232498 | 4/2002 |
| WO | WO-02074211 | 9/2002 |
| WO | WO-03/070133 | 8/2003 |
| WO | WO-03070133 | 8/2003 |
| WO | WO-2004/014472 | 2/2004 |
| WO | WO-2004012809 | 2/2004 |
| WO | WO-2005/110529 | 11/2005 |
| WO | WO-2010/045228 A3 | 4/2010 |
| WO | WO-2010/133704 A2 | 11/2010 |
| WO | WO-2011/005993 A1 | 1/2011 |

OTHER PUBLICATIONS

Non-Final Office Action received in U.S. Appl. No. 12/425,868, dated Nov. 25, 2011.
International Search Report and Written Opinion received in International Application No. PCT/US2011/041576, dated Sep. 19, 2011.
Non-Final Office Action received in U.S. Appl. No. 12/824,120, dated Jun. 8, 2012.
International Search Report and Written Opinion received in International Application No. PCT/US2007/083428 dated May 20, 2008.
Final Office Action received in U.S. Appl. No. 12/425,868, dated Jul. 6, 2012.

* cited by examiner

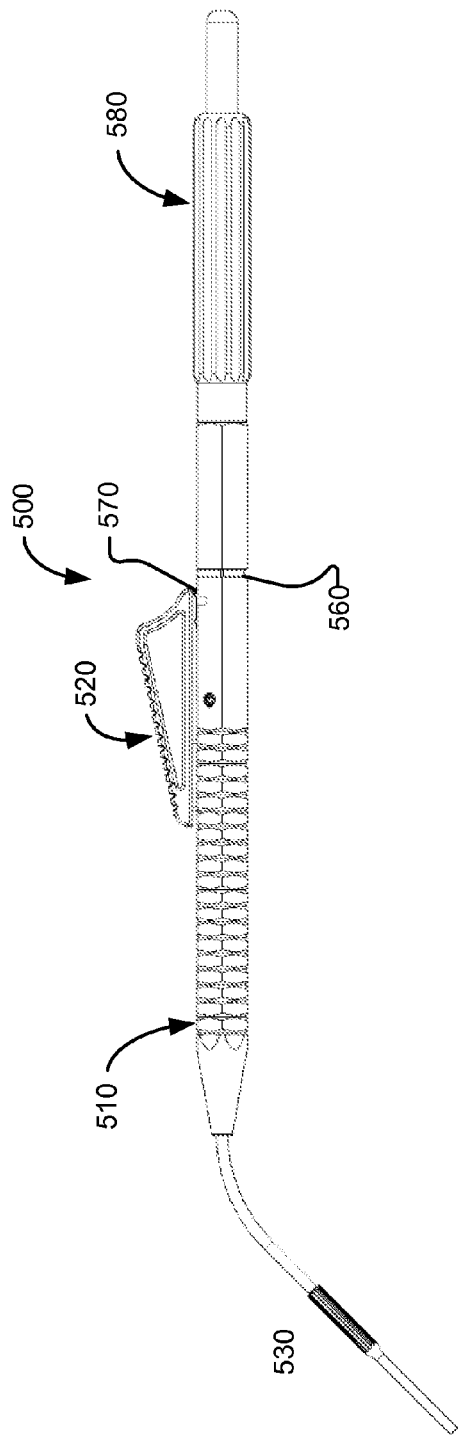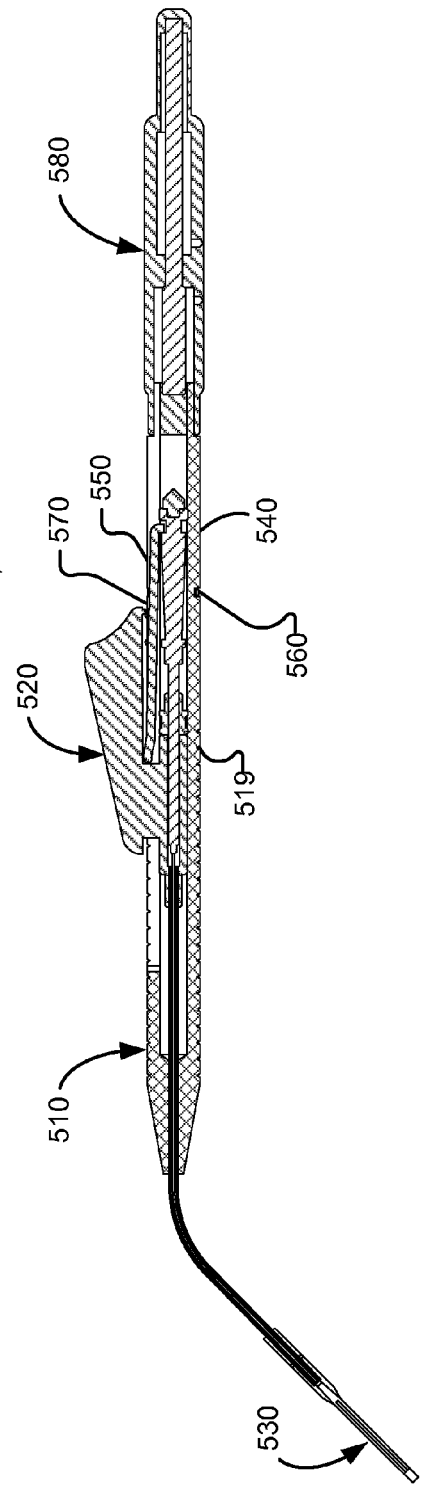

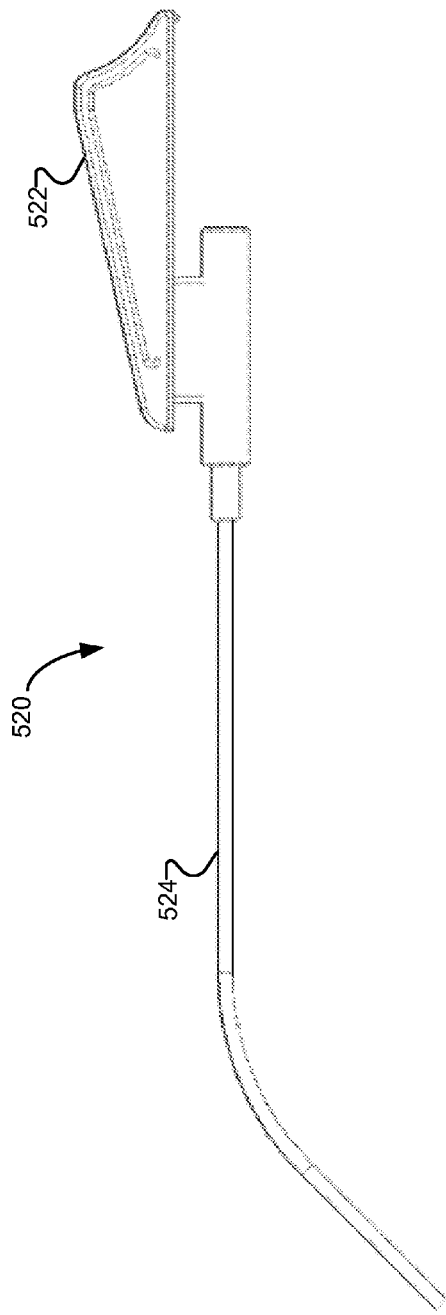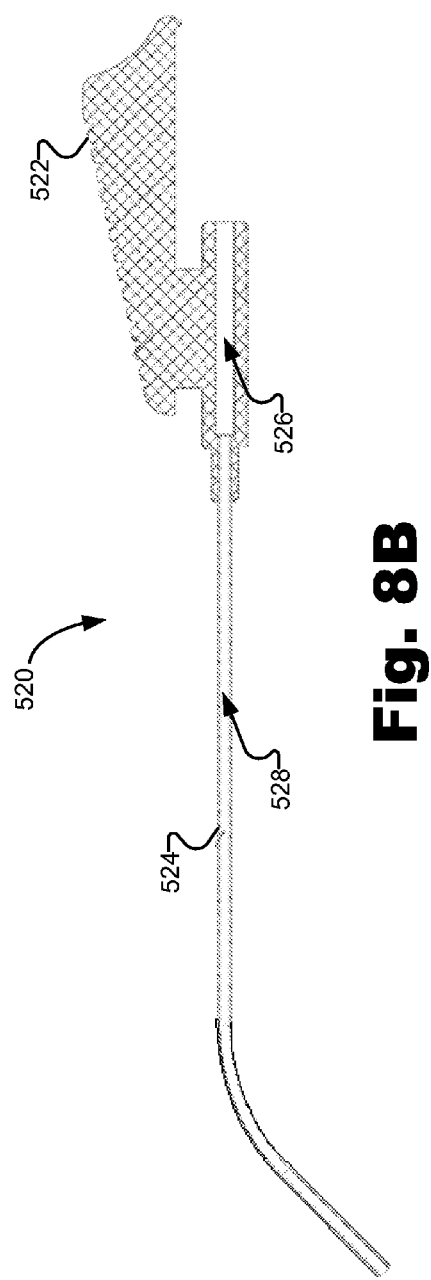

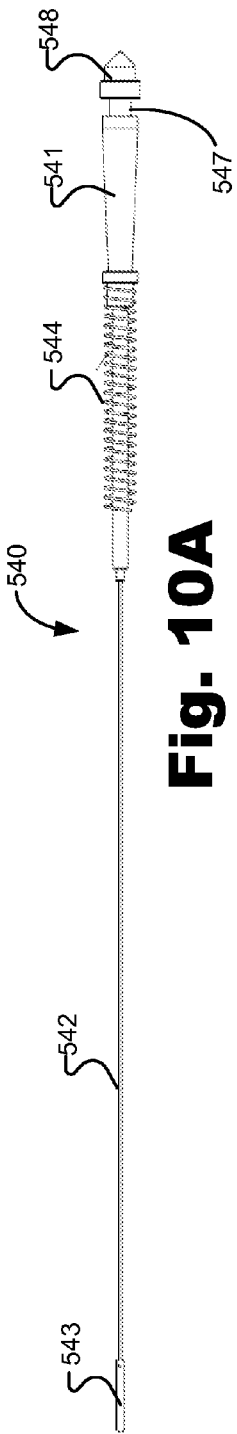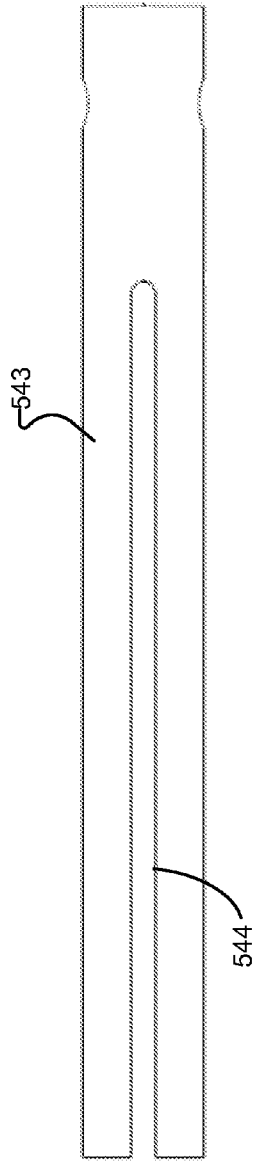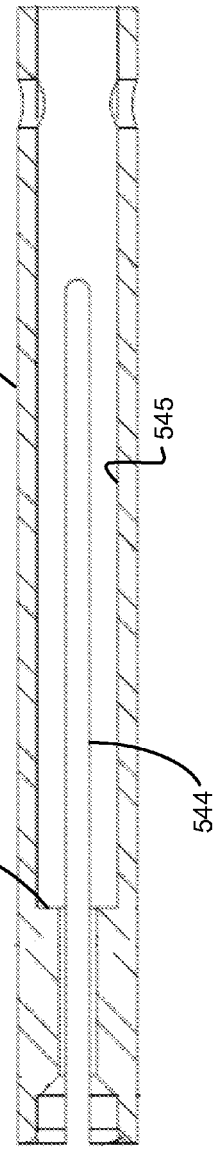

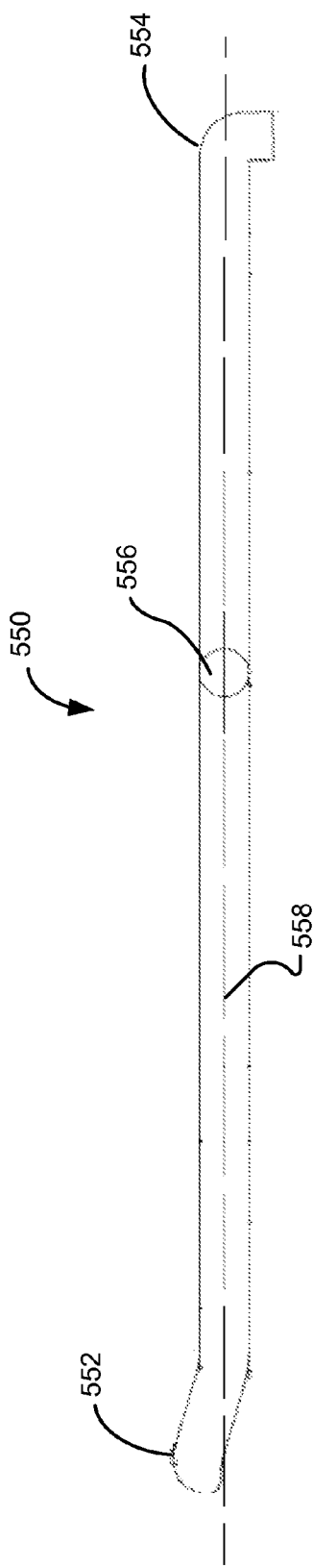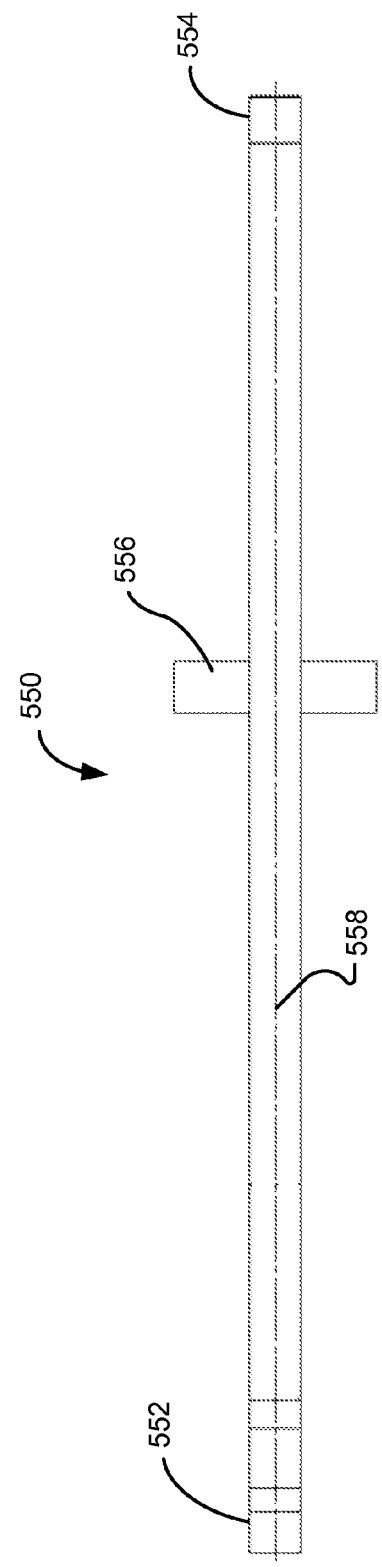
Fig. 11A
Fig. 11B

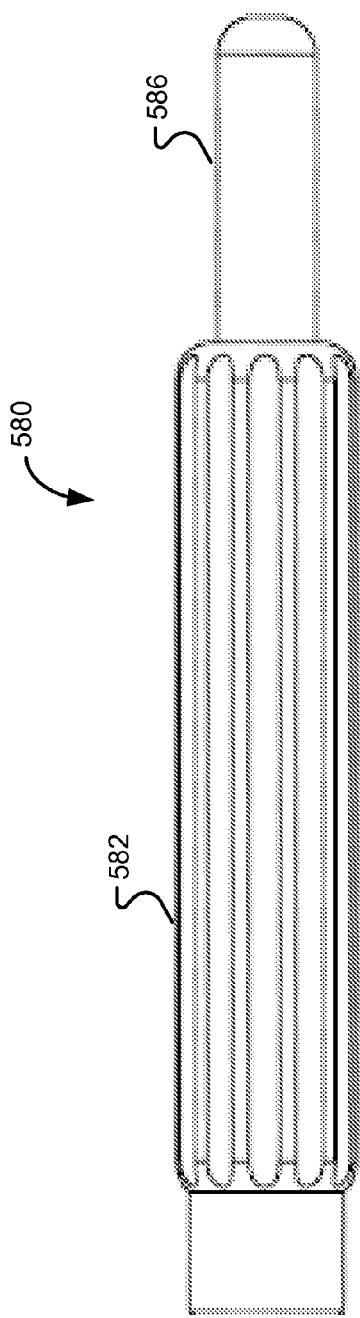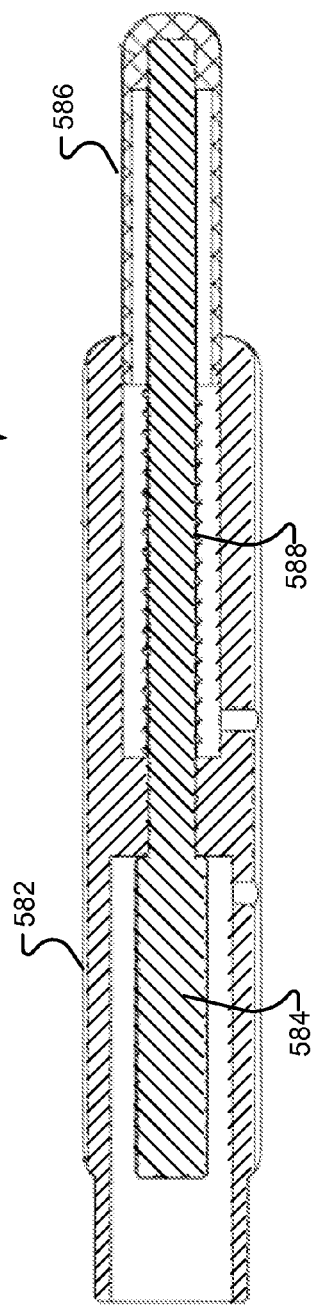
Fig. 14A
Fig. 14B

TOOLS, SYSTEMS, AND METHODS FOR INSERTING A PRE-CURVED ELECTRODE ARRAY PORTION OF A LEAD INTO A BODILY ORIFICE

BACKGROUND

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an electrode array may be implanted in the cochlea. Electrodes included on the electrode array form stimulation channels through which electrical stimulation pulses may be applied directly to auditory nerves within the cochlea. An audio signal may therefore be presented to a patient by translating the audio signal into electrical stimulation pulses and applying the stimulation pulses directly to auditory nerves within the cochlea via one or more of the electrodes.

The electrode array is often implanted within the scala tympani, one of three parallel ducts that make up the spiral-shaped cochlea. Electrode arrays that are implanted in the scala tympani typically include several separately connected stimulating electrode contacts longitudinally disposed on a thin, elongate, and flexible carrier. Such an electrode array is pushed into the scala tympani duct via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular application. To this end, various leads have been developed that have spiral-shaped pre-curved electrode array portions to better conform to the shape of the scala tympani and/or other auditory structures.

Unfortunately, many conventional insertion tools used to insert the pre-curved electrode array portion of a lead into the cochlea are cumbersome and difficult to use. For example, it is often difficult to release a lead from an insertion tool once the pre-curved electrode array portion of the lead has been inserted into the cochlea. In addition, a straightening member (e.g., a stylet) may be used to facilitate insertion of the pre-curved electrode array portion of a lead into the cochlea, and retracting the straightening member from the pre-curved electrode array portion may be difficult and tend to dislodge the electrode array portion out of position.

SUMMARY

An exemplary insertion tool configured to facilitate insertion of a pre-curved electrode array portion of a lead into a bodily orifice includes a handle assembly configured to facilitate handling of the insertion tool, a slider assembly configured to be actuated by a user to operate the insertion tool, an insertion assembly coupled to the handle assembly and comprising a holder member configured to removably couple to a lead, and a retractor assembly disposed at least partially within the handle assembly and configured to selectively couple to a straightening member inserted into the pre-curved electrode array portion and at least partially retract the straightening member from the pre-curved electrode array portion in response to actuation by the user of the slider assembly. The retractor assembly may comprise a spring-loaded retractor member configured to move from a distal position to a proximal position in response to actuation by the user of the slider assembly to at least partially retract the straightening member from the pre-curved electrode array portion.

An exemplary system comprises a lead including a pre-curved electrode array portion, a straightening member inserted into the pre-curved electrode array portion to retain the pre-curved electrode array portion in a straightened configuration, and an insertion tool configured to facilitate insertion of the pre-curved electrode array portion into a bodily orifice. The insertion tool includes a handle assembly configured to facilitate handling of the insertion tool, a slider assembly configured to be actuated by a user to operate the insertion tool, an insertion assembly coupled to the handle assembly and comprising a holder member configured to removably couple to the lead, and a retractor assembly disposed at least partially within the handle assembly and configured to selectively couple to the straightening member and at least partially retract the straightening member from the pre-curved electrode array portion in response to actuation by the user of the slider assembly. The retractor assembly may comprise a spring-loaded retractor member configured to move from a distal position to a proximal position in response to actuation by the user of the slider assembly to at least partially retract the straightening member from the pre-curved electrode array portion.

An exemplary method of inserting a pre-curved electrode array portion of a lead into a bodily orifice includes coupling the proximal portion of a straightening member inserted into the pre-curved electrode array portion to an insertion tool, moving a slider member of the insertion tool from a first position to a second position to retain the straightening member coupled to the insertion tool, guiding the pre-curved electrode array portion into the bodily orifice with the insertion tool, moving the slider member from the second position towards a third position to advance the pre-curved electrode array portion in a distal direction relative to the straightening member, and moving the slider member to the third position to release the spring-loaded retractor member to allow the spring-loaded retractor member to move from the distal position to the proximal position to at least partially retract the straightening member from the pre-curved electrode array portion.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 6A is a side view of the exemplary insertion tool of FIG. 5 according to principles described herein.

FIG. 6B is a cross-sectional side view of the exemplary insertion tool of FIG. 5 according to principles described herein.

FIG. 8A is a side view of an exemplary slider assembly of the exemplary insertion tool of FIG. 5 according to principles described herein.

FIG. 8B is a cross-sectional side view of the exemplary slider assembly of the FIG. 8A according to principles described herein.

FIG. 10A is a side view of an exemplary retractor assembly of the insertion tool of FIG. 5 according to principles described herein.

FIG. 10B is a side view of an exemplary collet member of the exemplary retractor assembly of FIG. 10A according to principles described herein.

FIG. 10C is a cross-sectional side view of the exemplary collet member of FIG. 10B according to principles described herein.

FIG. 11A is a side view of an exemplary rocker lever of the exemplary insertion tool of FIG. 5 according to principles described herein.

FIG. 11B is a top view of the exemplary rocker lever of FIG. 11A.

FIG. 14A is a side view of an exemplary plunger assembly of the insertion tool of FIG. 5 according to principles described herein.

FIG. 14B is a cross-sectional side view of the exemplary plunger assembly of FIG. 14A according to principles described herein.

Throughout the drawings, identical reference numbers may designate similar, but not necessarily identical, elements.

DETAILED DESCRIPTION

Figure 1:
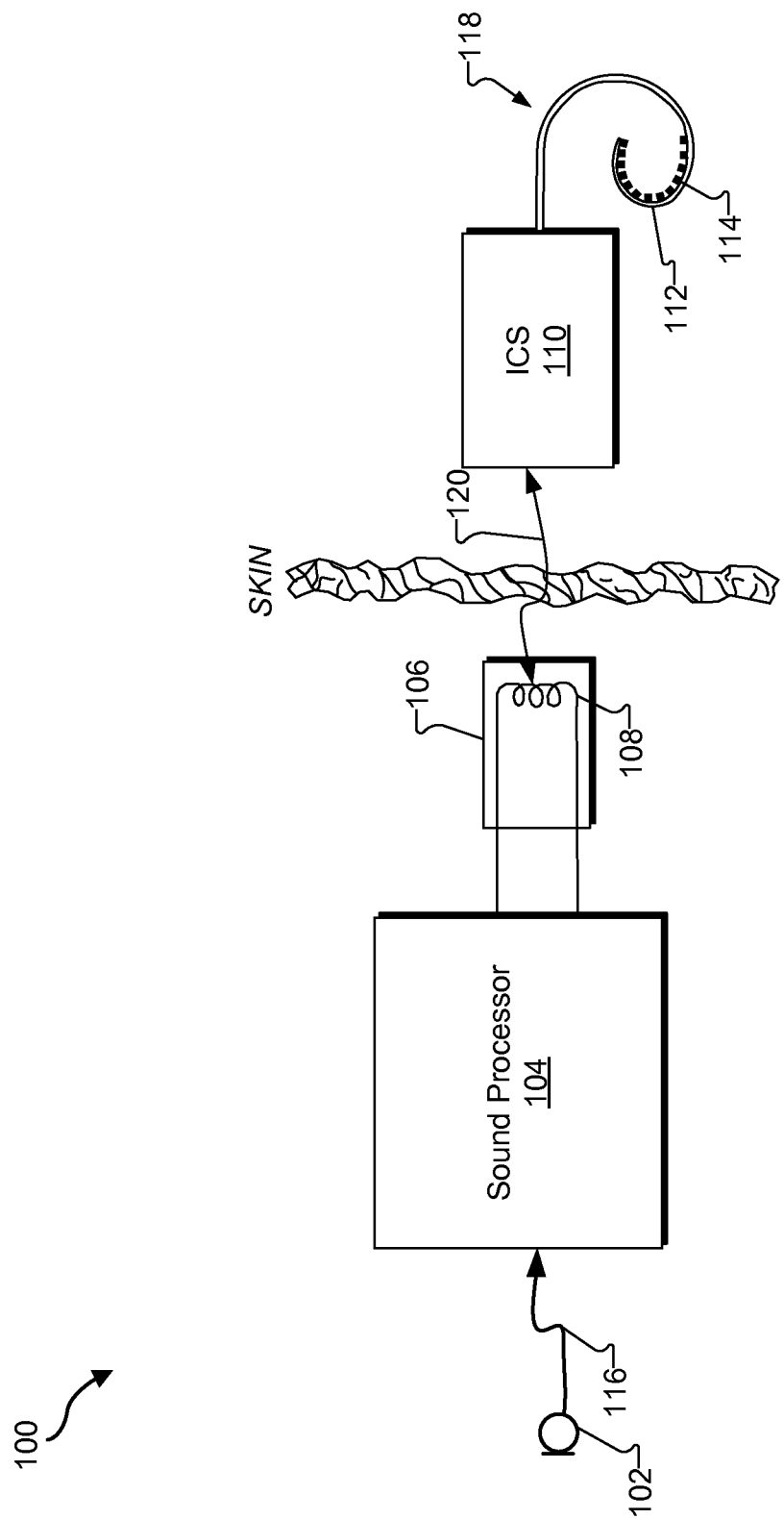
FIG. 1 illustrates an exemplary cochlear implant system according to principles described herein.

Exemplary insertion tools, systems, and methods for inserting a pre-curved electrode array portion of a lead into a bodily orifice are described herein. As used herein, the term "bodily orifice" refers to a duct of the cochlea, a surgically made opening or incision (e.g., a cochleostomy or facial recess) within the patient, or any other location within the patient. For illustrative purposes only, it will be assumed in the examples given that the insertion tools, systems, and methods described herein may be used to insert the pre-curved electrode array portion of the lead into a duct of the cochlea via a cochleostomy.

In some examples, an insertion tool includes a handle assembly, a slider assembly, an insertion assembly, a retractor assembly, and a plunger assembly. The handle assembly may be configured to facilitate handling of the insertion tool. The slider assembly may be configured to be actuated by a user to operate the insertion tool. The insertion assembly may include a holder member configured to removably couple to a lead. The retractor assembly may be configured to selectively couple to a straightening member inserted into the pre-curved electrode array portion of the lead and at least partially retract the straightening member from the pre-curved electrode array portion in response to actuation by the user of the slider assembly. The plunger assembly may be configured to reset the retractor assembly in response to user actuation of the plunger assembly.

A number of advantages are associated with the insertion tools, systems, and methods described herein. For example, the insertion tools described herein may facilitate insertion of a pre-curved electrode array portion of a lead that is in a straightened configuration into a duct of the cochlea and the corresponding movement of the pre-curved electrode array portion from the straightened configuration to a curved configuration to conform to the curvature of the cochlea. The insertion tools described herein may additionally or alternatively be used with either the right or left hand of a surgeon or other user to insert a pre-curved electrode array portion of a lead into either a right or left cochlea and are configured to not obstruct the view of the user while inserting the pre-curved electrode array portion into the cochlea. Moreover, the insertion tools described herein may facilitate selective coupling with a straightening member and one-handed retraction of the straightening member from a pre-curved electrode array portion of a lead. These advantages will be described in more detail below.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

FIG. 1 illustrates an exemplary cochlear implant system 100. Cochlear implant system 100 may include a microphone 102, a sound processor 104, a headpiece 106 having a coil 108 disposed therein, an implantable cochlear stimulator ("ICS") 110, and a lead 118 having a pre-curved electrode array portion 112 comprising a plurality of electrodes 114. Additional or alternative components may be included within cochlear implant system 100 as may serve a particular application.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented within a behind-the-ear ("BTE") unit, a portable speech processor ("PSP"), and/or any other sound processing unit as may serve a particular application. Exemplary components of sound processor 104 will be described in more detail below.

Sound processor 104 may be configured to transcutaneously transmit one or more control parameters and/or one or more power signals to implantable cochlear stimulator 110 with coil 108 by way of communication link 120. These control parameters may be configured to specify one or more stimulation parameters, operating parameters, and/or any other parameter as may serve a particular application. Exemplary control parameters include, but are not limited to, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and back-end dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 120. It will be understood that data communication link 120 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 114 included within pre-curved electrode array portion 112 of lead 118.

To facilitate application of the electrical stimulation generated by implantable cochlear stimulator 110, pre-curved electrode array portion 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Pre-curved electrode array portion 112 may comprise any number of electrodes 114 (e.g., sixteen) as may serve a particular application.

Figure 2:
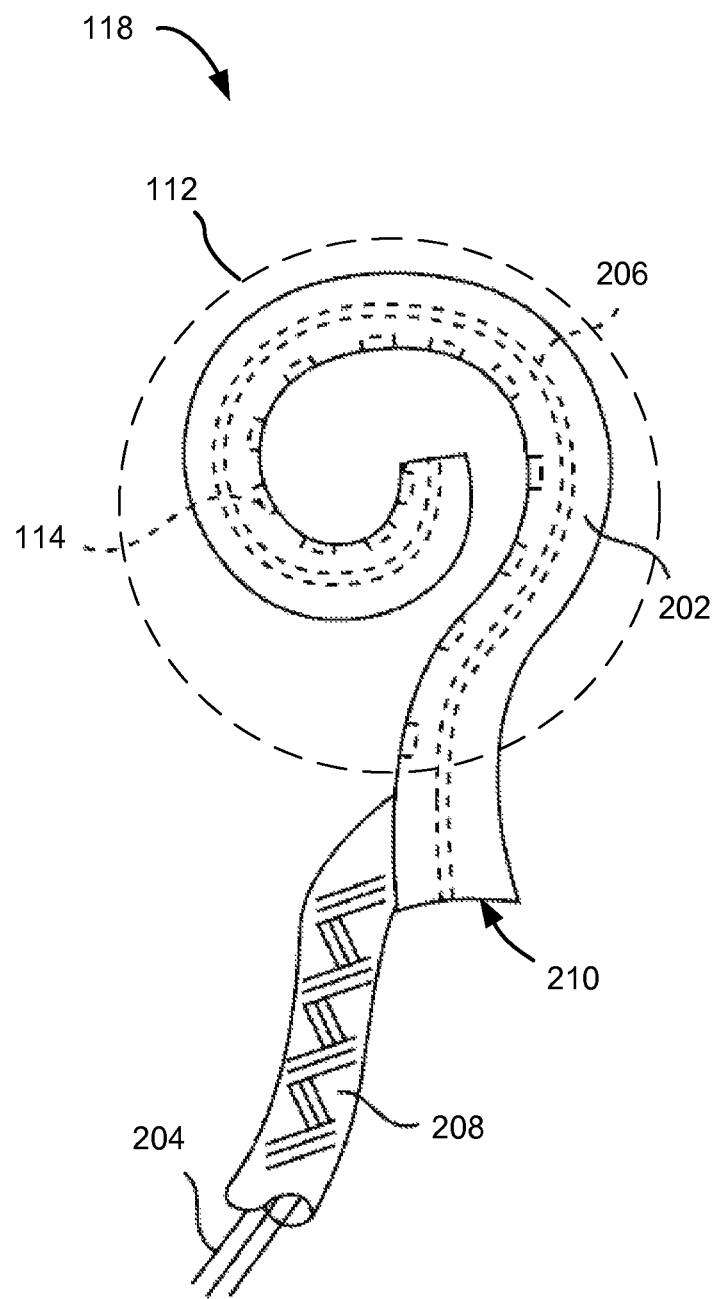
FIG. 2 illustrates an exemplary lead that has a pre-curved electrode array portion according to principles described herein.

FIG. 2 shows an exemplary lead 118 that has a pre-curved electrode array portion 112. Lead 118 may be substantially as shown and described in U.S. Pat. Nos. 4,819,647; 6,129,753; or 6,604,283, and in the U.S. patent application Ser. No. 12/823,380 entitled "COCHLEAR IMPLANT SYSTEM WITH REMOVABLE STYLET" to Gallegos et al. filed Jun. 25, 2010, each of which is incorporated herein by reference in its respective entirety.

As shown in FIG. 2, pre-curved electrode array portion 112 may have the same general curvature as that of a human cochlea. In some examples, pre-curved electrode array portion 112 includes an array of electrodes 114 (also referred to as "electrode contacts 114") disposed on an elongate flexible carrier 202 and connected to corresponding insulated wires 204. Elongate flexible carrier 202 of lead 118 may be made out of any suitable material such as, but not limited to, silicone rubber or plastic, and has a hole or lumen 206 passing at least partially therethrough. In some examples, carrier 202 is constructed so as to have a built-in bias or memory force which forces carrier 202 to naturally assume the curved configuration shown in FIG. 2. In addition, the material of the carrier 202 may be configured to allow carrier 202 to be straightened when loaded on a straightening member. Once inserted within the duct of a cochlea, the memory force of carrier 202 forces carrier 202 to return to the desired curvature (e.g., as shown in FIG. 2).

As shown in FIG. 2, a proximal end of carrier 202 is coupled to a lead body 208 through which wires 204 continue and connect to implantable cochlear stimulator 110. Implantable cochlear stimulator 110 is thus able to make electrical connection with each of the electrodes 114 through one or more of wires 204. In some examples, the electrodes 114 of pre-curved electrode array portion 112 are configured to be positioned along a medial electrode wall, i.e., the inside curve of carrier 202 such that they face the modiolus when implanted in the cochlea.

Lead 118 may also include a coupling portion 210 proximal of the electrode array portion 112. Coupling portion 210 may be configured to removably couple to and/or be pushed by one or more components of an insertion tool. For example, an insertion tool may removably couple to coupling portion 210 to guide lead 118 at least partially into a bodily orifice, such as a human cochlea. The insertion tool may also push coupling portion 210 to decouple lead 118 from the insertion tool and to further advance lead 118 into the bodily orifice.

Figure 3:
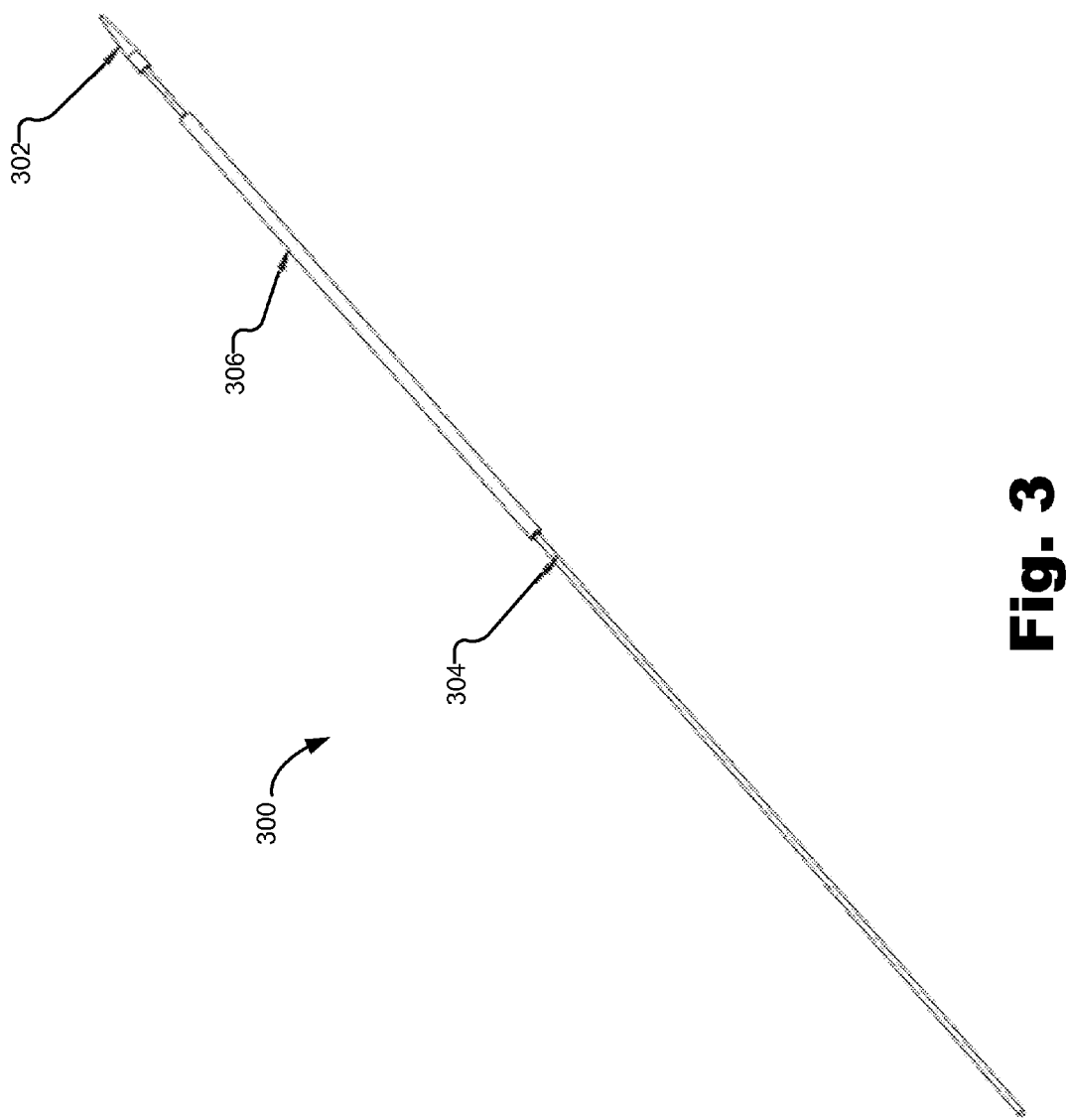
FIG. 3 is a perspective view of an exemplary straightening member that may be inserted into a pre-curved electrode array portion of a lead to retain the pre-curved electrode array portion in a straightened configuration according to principles described herein.

As mentioned, pre-curved electrode array portion 112 may be loaded onto a straightening member before being implanted within a duct of the cochlea. FIG. 3 is a perspective view of an exemplary straightening member 300 (e.g., a stylet) that may be used in accordance with the systems and methods described herein. As shown in FIG. 3, straightening member 300 may include a proximal portion 302 coupled to the proximal end of a substantially straight member 304 and a stiffening member 306 disposed over at least a portion of substantially straight member 304. Proximal portion 302 may be of any dimension to accommodate manual handling thereof and/or attachment of an insertion tool thereto. For example, proximal portion 302 may have a bullet-shape or substantially conical shape configured to be inserted into and coupled to a portion of an insertion tool, as will be described in more detail below. Substantially straight member 304 may be configured to be at least partially inserted into a lumen of a pre-curved electrode array portion of a lead to retain the pre-curved electrode array portion in a straightened configuration. As shown, substantially straight member 304 may have a rounded (e.g., a semispherical) distal tip to facilitate insertion into a pre-curved electrode array portion without damaging the pre-curved electrode array portion. Stiffening member 306 may be configured to provide any desired stiffness to substantially straight member 304 as may be desired for a particular implementation.

Straightening member 300 may be made out of any suitable material with sufficient stiffness so as to facilitate entry into the cochlea. For example, straightening member 300 may be made out of a metal (e.g., stainless steel or titanium), a metal alloy, a hard plastic, any other suitable material, and/or combinations thereof. In some examples, straightening member 300 may include a coating disposed thereon. The coating may be configured to be lubricious to reduce friction between straightening member 300 and other components (e.g., an insertion tool or lead 118). For example, the coating may be a polytetrafluoroethylene ("PTFE") coating.

Figure 4:
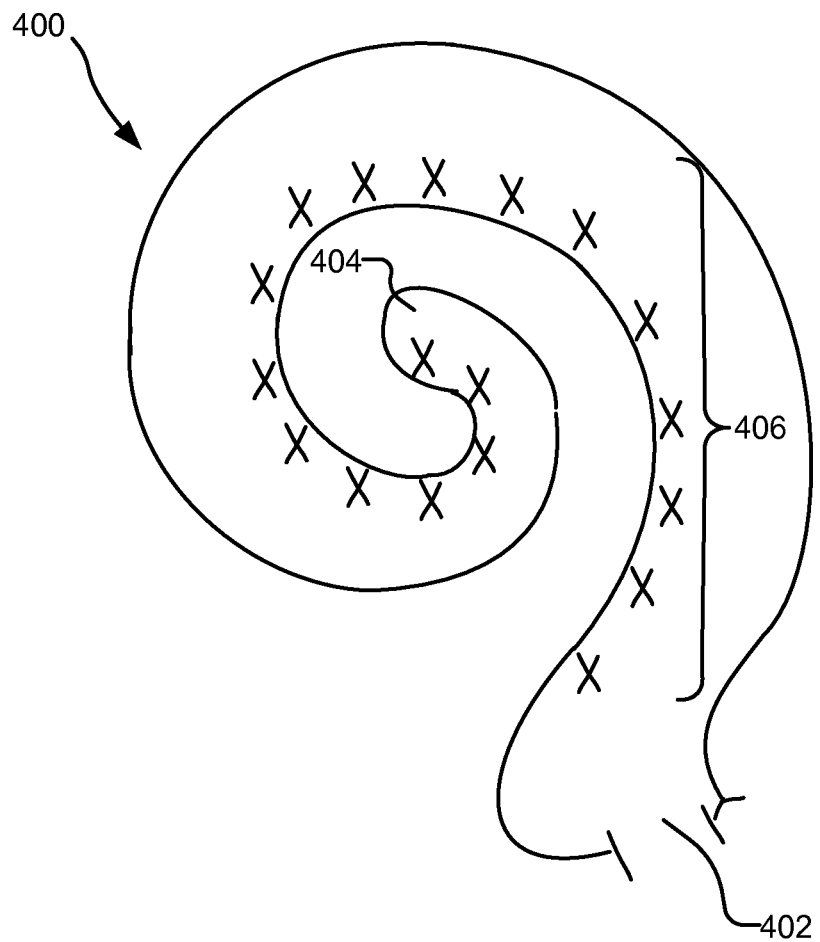
FIG. 4 illustrates a schematic structure of a human cochlea.

FIG. 4 illustrates a schematic structure of the human cochlea 400 into which pre-curved electrode array portion 112 may be inserted. As shown in FIG. 4, the cochlea 400 is in the shape of a spiral beginning at a base 402 and ending at an apex 404. Within the cochlea 400 resides auditory nerve tissue 406, which is denoted by Xs in FIG. 4. The auditory nerve tissue 406 is organized within the cochlea 400 in a tonotopic manner. Low frequencies are encoded at the apex 404 of the cochlea 400 while high frequencies are encoded at the base 402. Hence, each location along the length of the cochlea 400 corresponds to a different perceived frequency. System 100 may therefore be configured to apply electrical stimulation to different locations within the cochlea 400 (e.g., different locations along the auditory nerve tissue 406) to provide a sensation of hearing.

Figure 5:
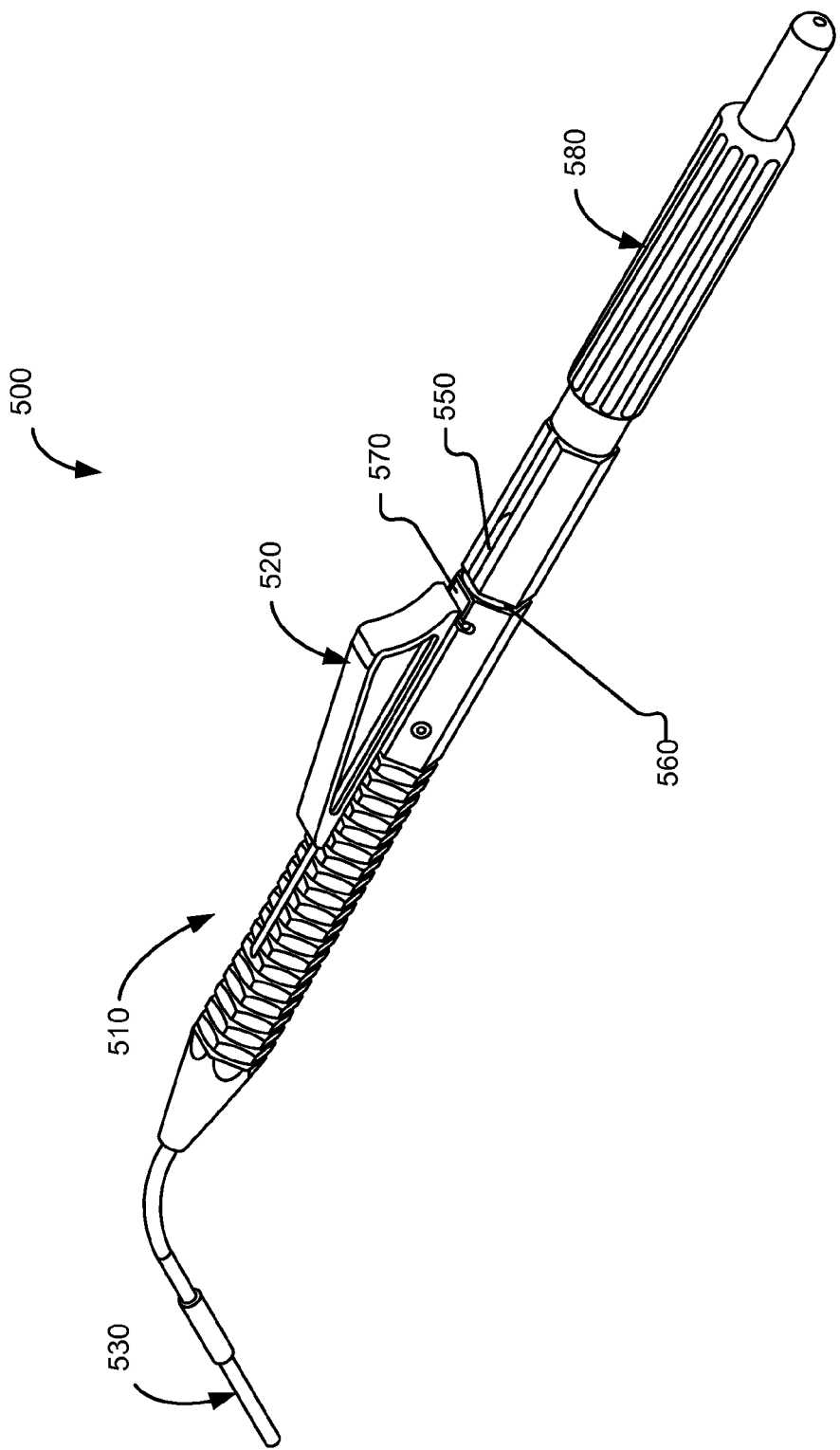
FIG. 5 is a perspective view of an exemplary insertion tool according to principles described herein.

FIG. 5 is a perspective view of an exemplary insertion tool 500 configured to facilitate insertion of a pre-curved electrode array portion of a lead into a bodily orifice according to principles described herein. Insertion tool 500 is shown in greater detail in FIG. 6A, which illustrates a side-view of insertion tool 500, and FIG. 6B, which illustrates a cross-sectional side view of insertion tool 500. As shown, insertion tool 500 may include a handle assembly 510, a slider assembly 520 disposed at least partially within and slidable relative to handle assembly 510, an insertion assembly 530 coupled to a distal end of handle assembly 510, a retractor assembly 540 disposed at least partially within handle assembly 510 and/or slider assembly 520, a rocker lever 550 rotatably coupled to handle assembly 510, a detent plate 570 coupled to handle assembly 510, a radial spring 560 disposed at least partially around handle assembly 510, and a plunger assembly 580 coupled to a proximal end of handle assembly 510. Each of the components of insertion tool 500 and the interaction between the components of insertion tool 500 will now be described in more detail.

Figure 7A:
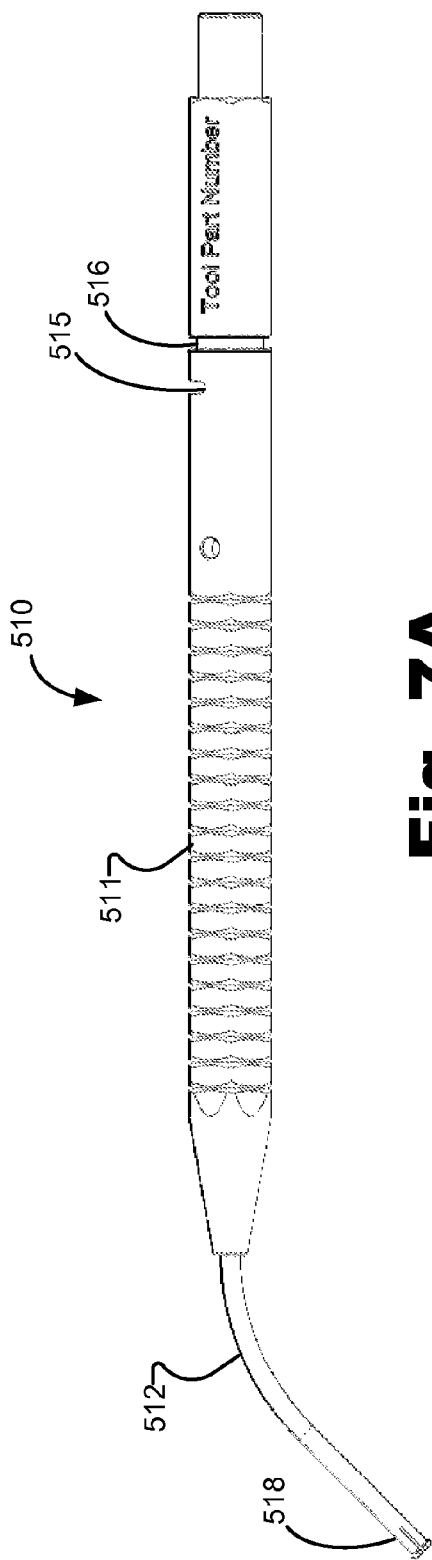
FIG. 7A is a side view of an exemplary handle assembly of the exemplary insertion tool of FIG. 5 according to principles described herein.
Figure 7B:
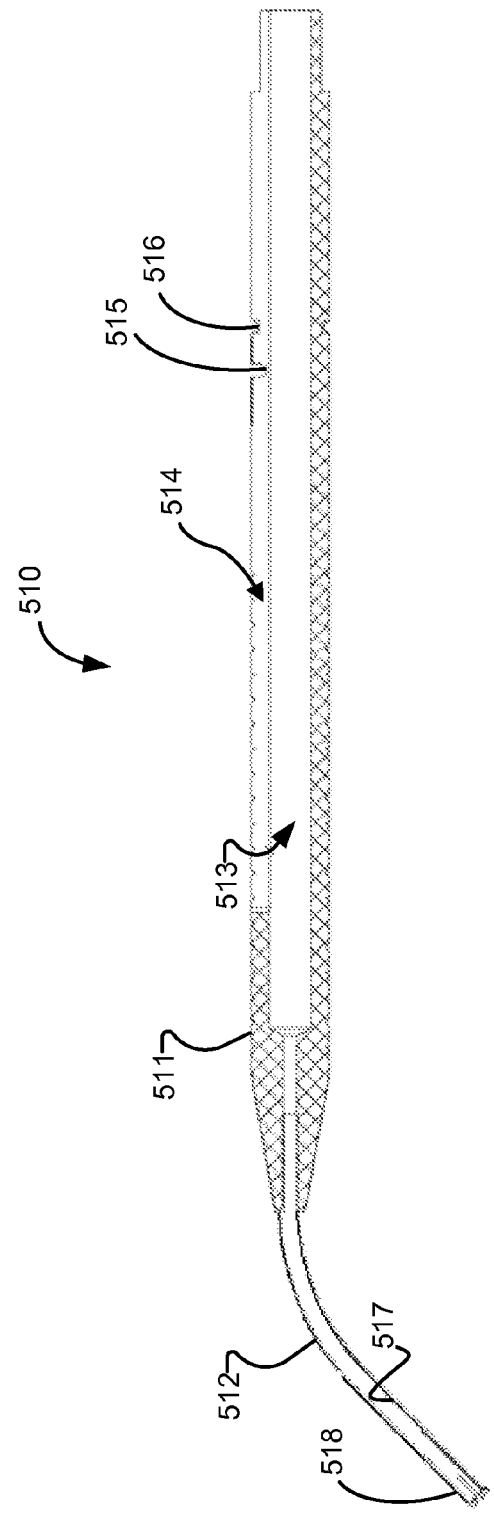
FIG. 7B is a cross-sectional side view of the exemplary handle assembly of FIG. 7A according to principles described herein.

As mentioned above, insertion tool 500 may include handle assembly 510. Handle assembly 510 may be configured to facilitate handling of insertion tool 500 by a user (e.g., a surgeon) and/or contain one or more other components of insertion tool 500. Handle assembly 510 is shown in more detail in FIG. 7A, which illustrates a side view of handle assembly 510, and FIG. 7B, which illustrates a cross-sectional side view of handle assembly 510.

As shown, handle assembly 510 may include a handle portion 511 and a guide tube 512 coupled to a distal end of the handle portion 511. Handle portion 511 may be configured to be gripped and/or handled by a user (e.g., a surgeon) of insertion tool 500 and may contain one or more other components of insertion tool 500. In some examples, handle portion 511 may have a hexagonal cross-section and knurling (e.g., grooves) to facilitate optimal gripping thereof by a user. Handle portion 511 may have a generally elongate shape and may be generally tubular with a lumen 513 extending at least partially therethrough. In this manner, one or more other components of insertion tool 500 (e.g., retractor assembly 540 or slider assembly 520) may be disposed at least partially within and/or slide relative to handle portion 511, as will be explained in more detail below.

Handle portion 511 may include one or more other features configured to facilitate coupling and/or interaction between handle portion 511 and one or more other components of insertion tool 500. For example, handle portion 511 may include a handle slot 514 extending along a length thereof and configured to allow one or more components of insertion tool to extend through handle slot 514 and/or move relative to handle portion 511 within handle slot 514. In certain examples, a portion of slider assembly 520 may pass through handle slot 514 and may be configured to slide along handle slot 514 relative to handle portion 511 to facilitate actuation of slider assembly 520 by a user. In some embodiments, rocker lever 550 may be at least partially disposed within handle slot 514 and move (e.g., rotate) relative to handle portion 511. Additionally or alternatively, handle portion 511 may include a rocker lever recess 515 configured to receive at least a portion of rocker lever 550 and facilitate rotation of rocker lever 550 relative to handle portion 511 and a radial spring recess 516 disposed at least partially around handle portion 511 and configured to receive radial spring 560, as will be explained in more detail below.

Guide tube 512 may be coupled to a distal end of handle portion 511. Guide tube 512 may be coupled to handle portion 511 in any suitable manner as may serve a particular implementation. For example, guide tube 512 may be welded, glued, or otherwise coupled to handle portion 511. Alternatively, guide tube 512 and handle portion 511 may be integrally formed together.

Guide tube 512 may be configured to at least partially contain one or more other components of insertion tool 500. For example, guide tube 512 may include a lumen 517 extending along at least a length thereof and in communication with lumen 513 of handle portion 511. In some examples, portions of slider assembly 520 and/or retractor assembly 540 may be at least partially disposed within lumen 517 and slidable relative to guide tube 512, as will be described in more detail below.

As shown, guide tube 512 may include a curved portion such that a distal portion 518 of guide tube 512 extends away from handle portion 511 at a predefined angle. Guide tube 512 may extend away from handle portion 511 at any suitable angle (e.g., approximately 45 degrees) as may serve a particular implementation. In certain embodiments, the angle of guide tube 512 may prevent handle portion 511 from obscuring the view of a user (e.g., a surgeon) as the user utilizes insertion tool 500 to insert a pre-curved electrode array portion of a lead into a bodily orifice.

In some examples, guide tube 512 may be configured to selectively couple to one or more components of insertion assembly 530. For example, distal portion 518 of guide tube 512 may be configured to selectively couple with insertion assembly 530. Distal portion 518 may include one or more features configured to facilitate coupling with insertion assembly 530. For example, distal portion 518 may include one or more slits therein configured to allow distal portion 518 to contract and/or expand as necessary to facilitate insertion of distal portion 518 into insertion assembly 530. Additionally or alternatively, distal portion 518 may include an annular ridge extending at least partially around distal portion 518 and configured to resist removal of distal portion 518 from insertion assembly 530. In certain examples, the one or more features of distal portion 518 may be configured to interface with corresponding features of insertion assembly 530 and/or to allow rotation of insertion assembly 530 relative to guide tube 512, as will be described in more detail below.

Guide tube 512 and/or handle portion 511 may be made out of any rigid material as may serve a particular implementation. For example, guide tube 512 and/or handle portion 511 may be made out of stainless steel, titanium, a hard plastic, any other suitable material, and/or combinations thereof as may serve a particular implementation.

Handle portion 511 and guide tube 512 are provided for illustrative purposes only and are not limiting. Handle assembly 510 may additionally or alternatively include any other components configured to facilitate handling or operation of insertion tool 500 as may serve a particular implementation.

Returning to FIGS. 5, 6A, and 6B, insertion tool 500 may include slider assembly 520 disposed at least partially within and slidable relative to handle assembly 510. Slider assembly 520 may be configured to be actuated by a user to operate insertion tool 500. For example, slider assembly 520 may be configured to be actuated by a user to advance a pre-curved electrode array portion of a lead into a bodily orifice and/or retract a straightening member from the pre-curved electrode array portion.

Slider assembly 520 is shown in greater detail in FIG. 8A, which illustrates a side view of slider assembly 520, and FIG. 8B, which illustrates a cross-sectional side view of slider assembly 520. As shown, slider assembly 520 may include a slider member 522 and a flexible pusher tube 524 coupled to a distal end of slider member 522. Pusher tube 524 may be coupled to slider member 522 in any suitable manner as may serve a particular implementation. For example, pusher tube 524 may be welded, glued, or otherwise coupled to slider member 522. Alternatively, pusher tube 524 and slider member 522 may be integrally formed together (e.g., molded together as a single piece of plastic).

Slider member 522 may be configured to be actuated (e.g., advanced in a distal direction relative to handle assembly 510 or retracted in a proximal direction relative to handle assembly 510) by a user to perform one or more of the functions of insertion tool 500 described herein. For example, slider member 522 may be at least partially disposed within and slidable relative to handle portion 511. In certain embodiments, a portion of slider member 522 may be disposed within lumen 513 of handle portion 511 while another portion of slider member 522 may extend through handle slot 514 and out of handle portion 511 to facilitate actuation of slider member 522 by a user.

Slider member 522 may include one or more features configured to facilitate actuation by a user. For example, slider member 522 may include grooves or ridges disposed along a surface thereof configured to promote friction between a user's fingers or thumb and slider member 522. Additionally or alternatively, the shape of slider member 522 may conform to the shape of a user's finger or thumb to facilitate gripping and actuation of slider member 522. Slider member 522 may include any other features configured to facilitate actuation of slider member 522 by a user.

In some examples, slider member 522 may be configured to slide relative to handle assembly 510 between a first position, a second position, and a third position. A user may selectively actuate slider member 522 to move slider member between the first position, the second position, and the third position to perform one or more operations of the insertion tool 500 (e.g., to selectively couple insertion tool 500 to a straightening member, to advance a pre-curved electrode array portion of a lead in a distal direction relative to insertion tool 500, or to at least partially retract a straightening member from a pre-curved electrode array portion of a lead), as will be explained in greater detail below.

Slider member 522 may be configured to contain one or more other components of insertion tool 500. For example, slider member 522 may include a lumen 526 extending therethrough, within which one or more other components of insertion tool 500 may be disposed. In some examples, retractor assembly 540 may be at least partially disposed through lumen 526 and slidable relative to slider member 522, as will be explained in more detail below.

Slider member 522 may be made out of any suitable material as may serve a particular implementation. For example, slider member 522 may be made out of one or more rigid materials, such as stainless steel, titanium, a hard plastic, any other suitable material, or combinations thereof.

Pusher tube 524 may be coupled to a distal end of slider member 522 and extend in a distal direction away from slider member 522. Pusher tube 524 may be coupled to slider member 522 in any suitable manner as may serve a particular implementation. For example, pusher tube 524 may be welded, glued, or otherwise coupled to slider member 522. Alternatively, pusher tube 524 and slider member 522 may be integrally formed together.

In some examples, pusher tube 524 may be configured to be disposed within and slidable relative to handle assembly 510. For example, pusher tube 524 may be configured to extend through at least a portion of guide tube 512. In certain examples, pusher tube 524 may be configured to extend beyond a distal end of guide tube 512 in response to actuation by a user of slider member 522.

A distal end of pusher tube 524 may be configured to engage and push one or more other components of insertion assembly 530. For example, pusher tube 524 may be configured to engage and advance one or more components of insertion assembly 530 to advance a pre-curved electrode array portion of a lead into a human cochlea, as will be described in more detail below.

Pusher tube 524 may be configured to contain one or more other components of insertion tool 500. For example, pusher tube 524 may include a lumen 528 extending therethrough and in communication with lumen 526 of slider member 522. In some examples, retractor assembly 540 may be disposed at least partially within lumen 526 and slidable relative to pusher tube 524, as will be explained in more detail below.

Pusher tube 524 may be made out of any suitable material as may serve a particular implementation. For example, pusher tube 524 may be made out of one or more semi-rigid or flexible materials, such as PTFE or any other suitable material as may serve a particular implementation.

Slider member 522 and pusher tube 524 are provided for illustrative purposes only and are not limiting. One will appreciate that slider assembly 520 may include additional or alternative elements and/or may exclude certain illustrated elements according to principles described herein.

Returning to FIGS. 5, 6A, and 6B, insertion tool 500 may include an insertion assembly 530 coupled to a distal end of handle assembly 510. In some examples, insertion assembly 530 may be configured to removably couple to a lead. Additionally or alternatively, insertion assembly 530 may be configured to assist in advancing a pre-curved electrode array portion of the lead off of a straightening member and into a cochlea.

Figure 9A:
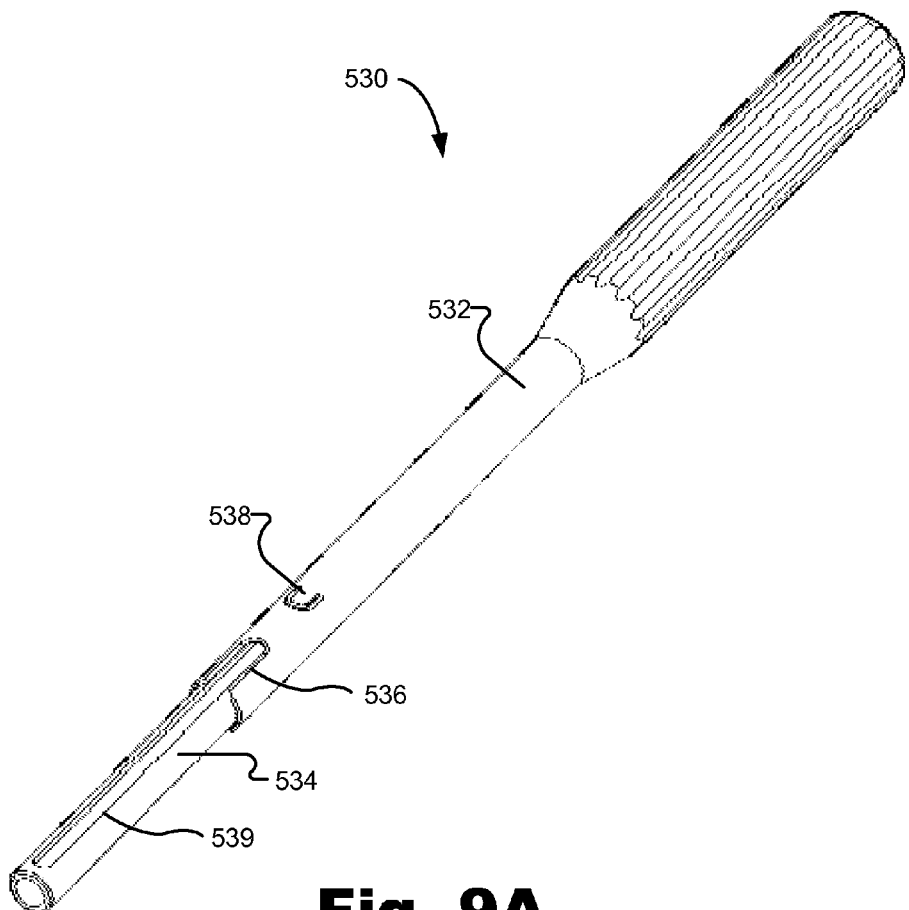
FIG. 9A is a perspective view of an exemplary insertion assembly of the exemplary insertion tool of FIG. 5 according to principles described herein.
Figure 9B:
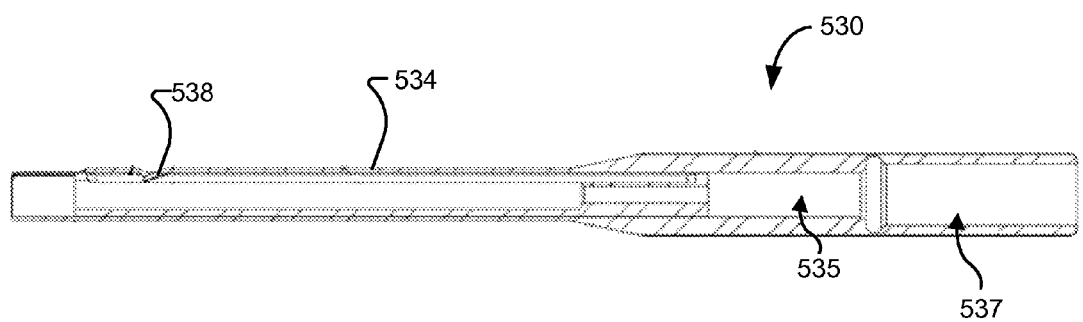
FIG. 9B is a cross-sectional side view of the exemplary insertion assembly of FIG. 9A according to principles described herein.

Insertion assembly 530 is shown in greater detail in FIG. 9A, which illustrates a side view of insertion assembly 530, and FIG. 9B, which illustrates a cross-sectional side view of insertion assembly 530. As shown, insertion assembly 530 may include a holder member 532 and an ejection member 534 disposed at least partially within and slidable relative to holder member 532.

In some examples, holder member 532 may be configured to removably couple to a lead having a pre-curved electrode array portion. For example, holder member 532 may include a lumen 535 with a distal portion thereof configured to receive a portion of a lead proximal of the electrode array portion of the lead. Additionally or alternatively, holder member 532 may include a distal slot 536 within a distal end thereof configured to hold a portion of a lead proximal of the electrode array portion of the lead. In some examples, distal slot 536 may be configured prevent relative rotation between holder member 532 and the lead.

Holder member 532 of insertion assembly 530 may be additionally configured to selectively couple to handle assembly 510 (shown in FIGS. 6A and 6B). For example, holder member 532 may be configured to couple to guide tube 512. In some examples, a proximal portion 537 (shown in FIG. 9B) of lumen 535 may be configured to receive and couple to distal portion 518 of guide tube 512 (shown in FIGS. 7A and 7B). For example, proximal portion 537 may be configured to receive and interface with distal portion 518 of guide tube 512. In certain examples, proximal portion 537 may have a size and shape that corresponds to the size and shape of distal portion 518 of guide tube 512. Additionally or alternatively, proximal portion 537 may include one or more features that correspond with features of distal portion 518. For example, proximal portion 537 may include an annular recess, as shown in FIG. 9A, configured to receive a corresponding annular ridge extending around distal portion 518. As a result, distal portion 518 may be inserted into and coupled to proximal portion 537 of holder member 532.

The coupling between proximal portion 537 and distal portion 518 may allow relative rotation between holder member 532 and guide tube 512. Accordingly, a user may rotate holder member 532 relative to guide tube 512 as desired to facilitate the selective use of insertion tool 500 to insert a pre-curved electrode array portion of a lead into a right or left cochlea. In some examples, holder member 532 may include knurling (e.g., ridges or grooves) and/or grit blasting along one or more surfaces thereof to facilitate gripping of holder member 532.

The features of holder member 532 and guide tube 512 may be configured to produce rotational friction between holder member 532 and guide tube 512 to resist inadvertent rotation of holder member 532 relative to guide tube 512. For example, distal portion 518 may be configured to engage the inner surface of proximal portion 537 thereby creating rotational friction between holder member 532 and guide tube 512. Additionally or alternatively, holder member 532 may include one or more friction tabs configured to extend radially inward and engage guide tube 512 in order to create rotational friction between holder member 532 and guide tube 512. Guide tube 512 may include a corresponding annular recess configured to receive and interface with the friction tabs. In some examples, the friction tabs of holder member 532 may be positioned within proximal portion 537 and may be configured to engage an annular recess within distal portion 518.

In certain embodiments, holder member 532 may be configured to limit relative movement between holder member 532 and ejection member 534. For example, holder member 532 may include a tab 538 configured to engage ejection member 534 to limit relative rotation and sliding between holder member 532 and ejection member 534. In some examples, tab 538 may be configured to extend at least partially into and interact with an ejection member slot 539 extending along a length of ejection member 534. Ejection member slot 539 may extend along substantially the entire length of ejection member 534 and may have closed longitudinal ends. As a result, interaction between tab 538 and ejection member slot 539 may limit the distance ejection member 534 may slide relative to holder member 532 and may prevent ejection member 534 from sliding entirely out of holder member 532. The length of ejection member slot 539 may be configured as desired to suit a particular implementation. For example, the length of ejection member slot 539 may be configured to allow ejection member 534 to extend a predetermined length out a distal end of holder member 532. In some examples, this predetermined length may be configured to achieve a desired advancement of a pre-curved electrode array portion of a lead relative to holder member 532.

Ejection member 534 may be configured to advance a lead having a pre-curved electrode array portion in a distal direction relative to holder member 532. For example, ejection member 534 may be configured to slide relative to holder member 532 between an extended position, as shown in FIG. 9A, and a retracted position, as shown in FIG. 9B. In some examples, pusher tube 524 of slider assembly 520 may be configured to engage and move ejection member 534 from the retracted position to the extended position in response to actuation of slider member 522 by a user. Ejection member 534 may, in turn, move the lead off of holder member 532 and/or at least partially move the pre-curved electrode array portion of the lead off of a straightening member inserted in the pre-curved electrode array portion to advance the pre-curved electrode array into a cochlea.

Holder member 532 and/or ejection member 534 may be made out of any rigid material as may serve a particular implementation. For example, holder member 532 and/or ejection member 534 may be made out of stainless steel, titanium, a hard plastic, any other suitable material, and/or combinations thereof as may serve a particular implementation.

Returning to FIG. 6B, as shown, insertion tool 500 may include a retractor assembly 540 disposed at least partially within and slidable relative to handle assembly 510 and/or slider assembly 520. Retractor assembly 540 may be configured to selectively couple to a straightening member inserted into a pre-curved electrode array portion of a lead and at least partially retract the straightening member from the pre-curved electrode array portion in response to actuation by a user of slider assembly 520.

Retractor assembly 540 is shown in greater detail in FIG. 10A, which illustrates a side view of retractor assembly 540. As shown, retractor assembly 540 may include a retractor member 541, a retractor wire 542 coupled to and extending from a distal end of retractor member 541, a collet member 543 coupled to a distal end of retractor wire 542, and a spring member 544 coupled to retractor member 541. Retractor member 541, retractor wire 542, collet member 543, and/or spring member 544 may be coupled together in any suitable manner as may serve a particular implementation. For example, retractor member 541, retractor wire 542, collet member 543, and/or spring member 544 may be welded, glued, or otherwise coupled together. Alternatively, retractor member 541, retractor wire 542, collet member 543, and/or spring member 544 may be integrally formed together.

Retractor assembly 540 may be configured to selectively couple to a straightening member. For example, collet member 543 may be configured to selectively couple to proximal portion 302 of straightening member 300. Collet member 543 is shown in more detail in FIG. 10B, which illustrates a side view of collet member 543, and in FIG. 10C, which illustrates a cross-sectional side view of collet member 543. As shown, collet member 543 may have a generally tubular configured with a lumen 545 extending at least partially therethrough. Collet member 543 may be configured to selectively expand to couple to straightening member 300 (e.g., to engage proximal portion 302 of straightening member 300). For example, collet member 543 may include one or more splits 544 extending from a distal end of collet member 543 along a length of collet member 543. Splits 544 may be configured to allow the distal end of collet member 543 to expand to receive proximal portion 302 of straightening member 300. As a result, proximal portion 302 of straightening member 300 may be inserted into lumen 545.

Insertion of straightening member 300 into lumen 545 may be accomplished by advancing proximal portion 302 in a proximal direction relative to and into collet member 543. Insertion of proximal portion 302 into collet member 543 may cause collet member 543 to expand with the sides thereof separating to receive proximal portion 302 into lumen 545. Once proximal portion 302 is fully within lumen 545, the sides of collet member 543 may return to their unexpanded position to retain proximal portion 302 within lumen 545. To this end, collet member 543 may include a ledge 546 within lumen 545 configured to resist removal of proximal portion 302 from lumen 545. Ledge 546 may form a portion of lumen 545 having a smaller inner diameter than the remainder of lumen 545. As a result, once proximal portion 302 moves past ledge 546, the sides of collet member 543 may return to their unexpanded position and ledge 546 may prevent or resist removal of proximal portion 302 from lumen 545.

Figure 16A:
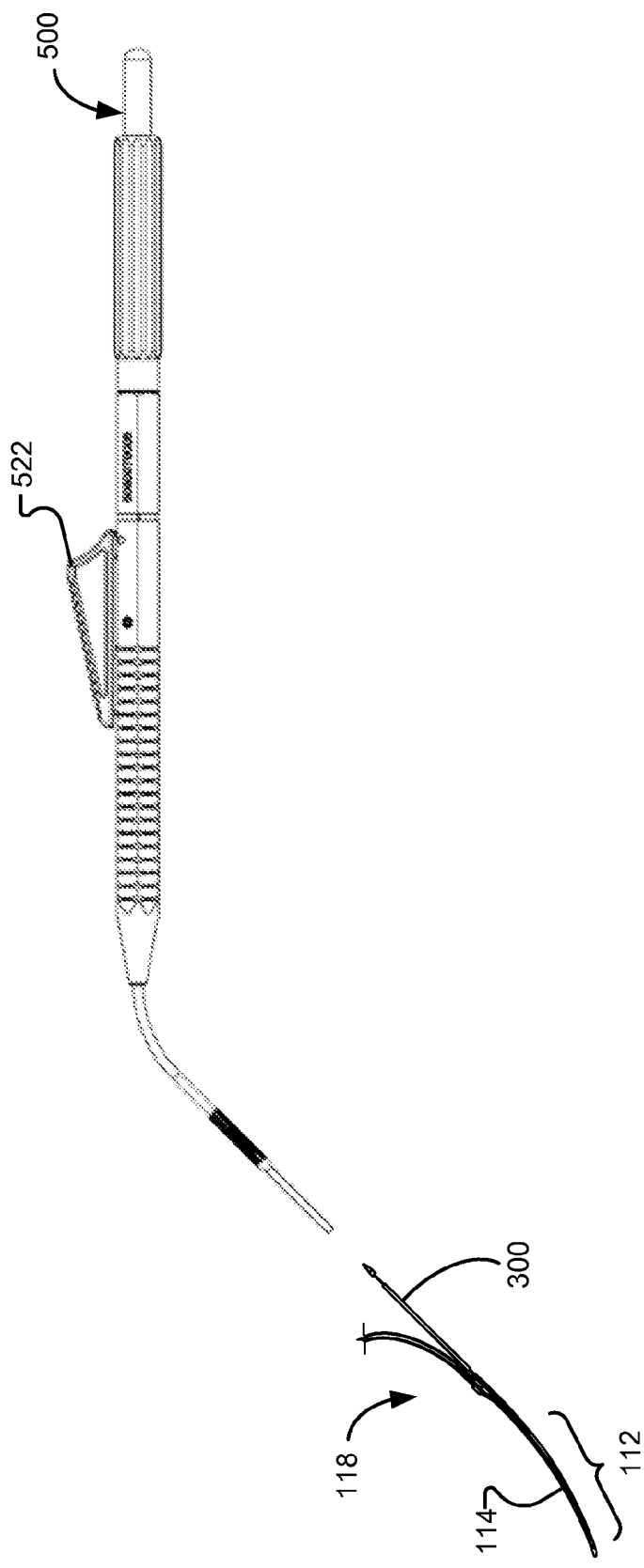
FIG. 16A shows an exemplary straightening member being coupled to an exemplary insertion tool according to principles described herein.
Figure 16B:
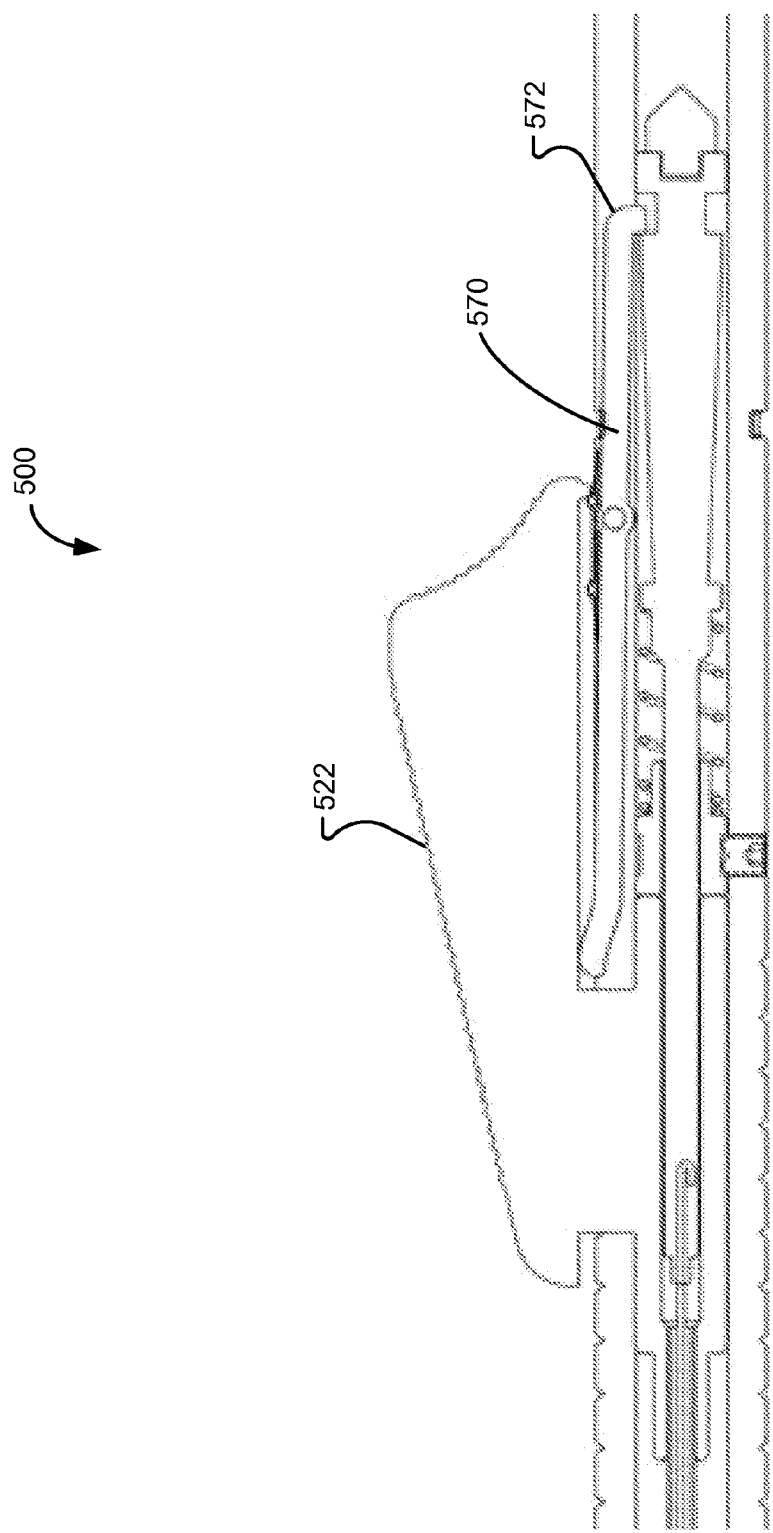
FIG. 16B shows the exemplary insertion tool of FIG. 16A with an exemplary slider member in a first position according to principles described herein.

In certain examples, interaction between collet member 543 and other components of insertion tool 500 may assist in coupling straightening member 300 to collet member 543. For example, pusher tube 524 may be configured to be selectively disposed around collet member 543 to prevent expansion of collet member 543 after proximal portion 302 is inserted into lumen 545. In certain embodiments, when slider member 522 is in a first position, the distal end of pusher tube 524 may be positioned proximal of collet member 543 to allow collet member 543 to expand to receive proximal portion 302. After proximal portion 302 is inserted into collet member 543, a user may actuate slider member 522 to move slider member 522 from the first position to a second position and to move a distal portion of pusher tube 524 over collet member 543 (as shown in FIG. 16F). As a result, pusher tube 524 may prevent further expansion of collet member 543 and/or inadvertent removal of proximal portion 302 from collet member 543, as will be described in more detail below.

After collet member 543 is coupled to the straightening member, retractor assembly 540 may be configured to at least partially retract the straightening member from the pre-curved electrode array portion of the lead. For example, retractor member 541, retractor wire 542, and collet member 543 may be configured to be slidable relative to handle assembly 510 and/or slider assembly 520 between a distal position and a proximal position to at least partially retract the straightening member from the pre-curved electrode array portion. In some examples, retractor member 541 may be configured to move from the distal position to the proximal position in response to actuation by a user of slider assembly 520. For example, as will be explained in more detail below, retractor member 541 may be retained in a distal position by one or more other components of insertion tool 500. While retractor member 541 is retained in the distal position, spring member 544 may be configured to store sufficient energy (e.g., in a compressed position) to move retractor member 541 from the distal position to the proximal position. Upon release of retractor member 541, spring member 544 may release the stored energy (e.g., elongate) to move retractor member 541 and, as a result, retractor wire 542 and collet member 543 from the distal position to the proximal position to at least partially retract a straightening member coupled to collet member 543 from the pre-curved electrode array portion. In some examples, a distal end of spring member 544 may be fixed relative to handle assembly 510 to facilitate movement of retractor member 541. For example, a distal end of spring member 544 may be connected to a sleeve member (e.g., sleeve member 519, FIG. 6B) coupled to handle portion 511.

Retractor member 541 may include an annular recess 547 configured to be selectively engaged by one or more other components of insertion tool 500 to retain retractor member 541 in the distal position, as will be explained in more detail below. Retractor member 541 may also include a shock absorber 548 configured to absorb energy created by contact between retractor assembly 540 and one or more other components of insertion tool 500, as will be described in more detail below. In some examples, shock absorber 548 may include or be replaced by a rubber bumper or an air dampening mechanism (e.g., an air cylinder) configured to dampen movement by retractor member 541.

In an alternative example, straightening member 300 may be integrated into retractor assembly 540. For example, straightening member 300 may be coupled during manufacturing to a distal end of retractor member 541.

Retractor member 541, retractor wire 542, collet member 543, and/or spring member 544 may be made out of any suitable material as may serve a particular implementation. For example, retractor member 541, retractor wire 542, collet member 543, and/or spring member 544 may be made out of stainless steel, titanium, a hard plastic, any other suitable material, and/or combinations thereof.

Returning to FIGS. 5, 6A, and 6B, insertion tool 500 may include a rocker lever 550 rotatably coupled to handle assembly 510 (e.g., to handle portion 511). Rocker lever 550 may be configured to selectively engage retractor member 541 to retain retractor member 541 in a distal position and, in response to actuation by a user of slider member 522, release retractor member 541 to move from the distal position to the proximal position to at least partially retract a straightening member from a pre-curved electrode array portion of a lead.

Rocker lever 550 is shown in more detail in FIG. 11A, which illustrates a side view of rocker lever 550, and FIG. 11B, which illustrates a top view of rocker lever 550. As shown, rocker lever 550 may be generally elongate in shape and may include a distal portion 552, a proximal portion 554, and an axle 556. In some examples, rocker lever 550 may extend generally along a longitudinal axis 558.

Distal portion 552 may be configured to be engaged by slider member 522 to partially rotate rocker lever 550 about axle 556. For example, distal portion 552 may angle upwards away from longitudinal axis 558. In this manner, distal portion 552 may extend upwards out of handle portion 511 so as to be engaged by slider member 522, as will be explained in more detail below.

Proximal portion 554 may be configured to engage retractor member 541. For example, proximal portion 554 may include a bend in rocker lever 550 extending away from longitudinal axis 558 at approximately a right angle and may configured to engage (e.g., insert into) annular recess 547 of retractor member 541 to retain retractor member 541 in a distal position.

Rocker lever 550 may be configured to partially rotate about axle 556. For example, axle 556 may be configured to be disposed within and rotate relative to rocker lever recess 515 of handle portion 511. As a result, rocker lever 550 may partially rotate in a first rotational direction to engage retractor member 541 with proximal portion 554 to retain retractor member 541 in a distal position. Additionally or alternatively, slider member 522 may be configured to engage distal portion 552 to partially rotate rocker lever 550 in a second rotational direction opposite the first rotational direction causing proximal portion 554 to disengage and release retractor member 541, as will be explained in more detail below.

Rocker lever 550 may be made out of any suitable material as may serve a particular implementation. For example, rocker lever 550 may be made out of one or more rigid materials, such as stainless steel, titanium, a rigid plastic, any other suitable rigid material, or combinations thereof as may serve a particular implementation.

Returning to FIGS. 5, 6A, and 6B, insertion tool 500 may include a radial spring 560 disposed at least partially around handle assembly 510. Radial spring 560 may be configured to engage rocker lever 550 and move rocker lever 550 into engagement with retractor member 541. For example, radial spring 560 may be configured to apply a constant force on rocker lever 550 to rotate rocker lever 550 to engage retractor member 541 with proximal portion 554. The force applied by radial spring 560 may be selectively overcome by actuation of slider member 522 by a user, thereby partially rotating rocker lever 550 in the opposite direction to disengage and release retractor member 541.

Figure 12:
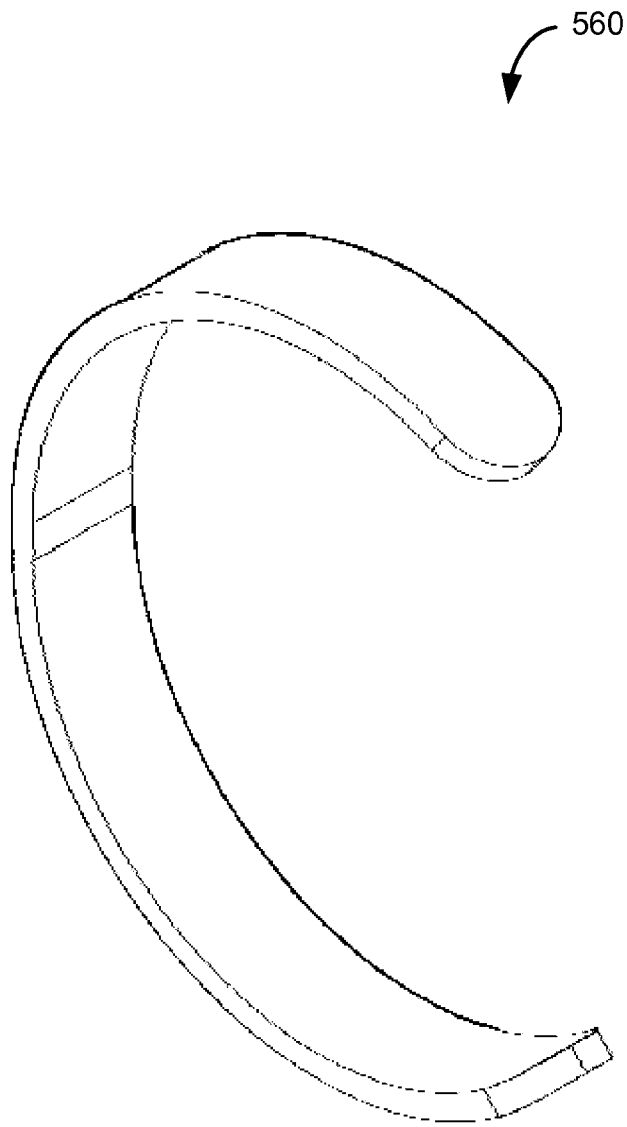
FIG. 12 is a perspective view of an exemplary radial spring of the exemplary insertion tool of the FIG. 5 according to principles described herein.

Radial spring 560 is shown in greater detail in FIG. 12. As shown, radial spring 560 may have a C-shaped configuration and may be configured to extend around at least a portion of handle portion 511. In some examples, radial spring may be configured to be disposed within radial spring recess 516 of handle portion 511.

Additionally or alternatively, radial spring 560 may be configured to have elastic properties. For example, radial spring 560 may be configured to elastically expand when rocker lever 550 is engaged and rotated by slider member 522 (e.g., to release retractor member 541) and then elastically contract when slider member 522 disengages rocker lever 552 to return rocker lever 550 to its original position (e.g., to engage retractor member 541).

Radial spring 560 may be made out of any suitable material as may serve a particular implementation. For example, radial spring 560 may be made out of one or more elastic materials, such as stainless steel, titanium, any other suitable material, or combinations thereof as may serve a particular implementation. In certain embodiments, the material of radial spring 560 may be spring tempered.

Returning to FIGS. 5, 6A, and 6B, insertion tool 500 may include a detent plate 570. Detent plate 570 may be configured to provide tactile feedback to a user (e.g., a surgeon) as the user actuates slider assembly 520. For example, detent plate 570 may be configured to provide tactile feedback to the user when the slider member 522 is in the first position and/or the second position.

Figure 13:
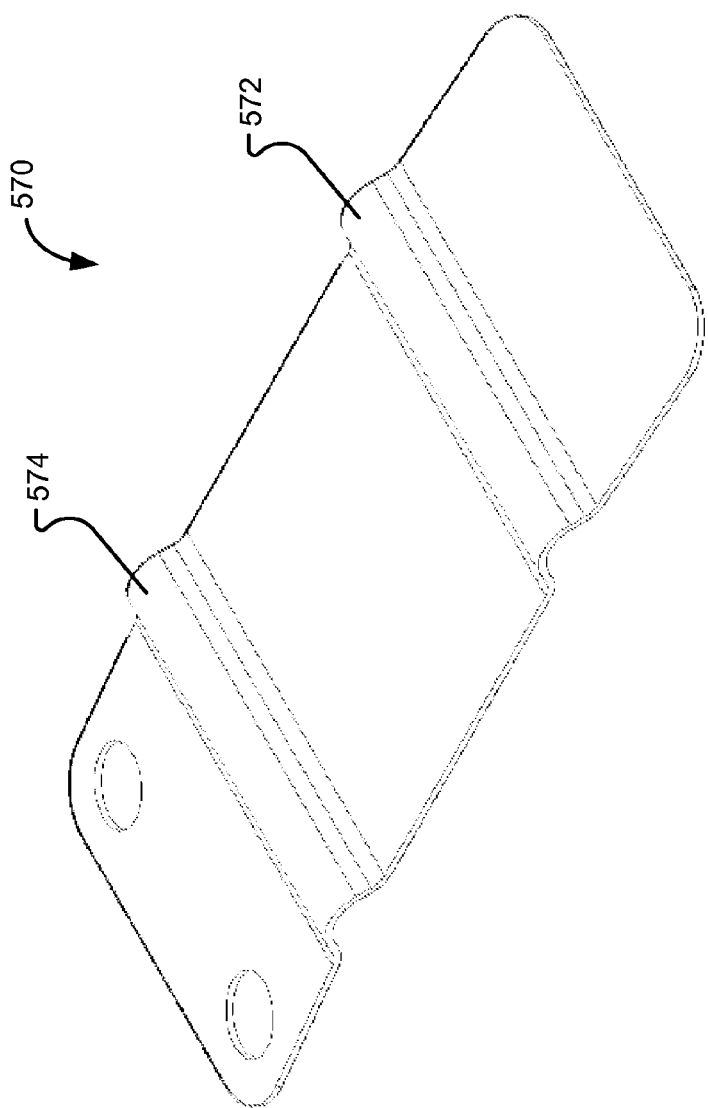
FIG. 13 is a perspective view of an exemplary detent plate of the exemplary insertion tool of FIG. 5 according to principles described herein.

Detent plate 570 is shown in greater detail in FIG. 13. As shown, detent plate may be coupled to handle portion 511 (e.g., by fastening, welding, or gluing). In some examples, detent plate 570 may define a first detent 572 and a second detent 574. First detent 572 may be configured to provide tactile feedback to a user when slider member 522 is in a first position. For example, slider member 522 may engage first detent 572 when in the first position. In some examples, the engagement between the slider member 522 and first detent 572 may at least partially resist movement of slider member 522 from the first position towards the second position. Second detent 574 may be configured to provide tactile feedback to a user when slider member 522 is in a second position. For example, slider member 522 may engage second detent 524 when in the second position. In some examples, the engagement between the slider member 522 and second detent 524 may at least partially resist movement of slider member 522 from the second position towards the third position. As a result, detent plate 570 may allow a user to feel when slider member 522 is in either the first position or the second position.

Detent plate 570 may be made out of any rigid or semi-rigid material as may serve a particular implementation. For example, detent plate 570 may be made out of stainless steel, titanium, a hard plastic, any other suitable material, and/or combinations thereof as may serve a particular implementation.

Returning to FIGS. 5, 6A, and 6B, insertion tool 500 may include a plunger assembly 580. Plunger assembly 580 may be configured to couple to a proximal end of handle assembly 510 and may be configured to be actuated by a user to reset retractor assembly 540 from a proximal position to a distal position.

Plunger assembly 580 is shown in greater detail in FIG. 14A, which illustrates a side view of plunger assembly 580, and 14B, which illustrates a cross-sectional side view of plunger assembly 580. As shown, plunger assembly 580 may include a plunger housing 582, a plunger member 584 disposed at least partially through and slidable relative to plunger housing 582, a button member 586 disposed at least partially through and slidable relative to plunger housing 582, and a spring member 588 with a distal end coupled to plunger housing 582 and a proximal end coupled to button member 586.

Plunger housing 582 may be configured to couple to handle portion 511 and at least partially house plunger member 584, button member 586, and/or spring member 588. For example, plunger housing 582 may include a lumen 583 extending along a length thereof and configured to at least partially house plunger member 584, button member 586, and/or spring member 588. In some examples, plunger housing 582 may include a plurality of grooves in a surface thereof to facilitate gripping by a user.

Plunger member 584 may be configured to engage and reset retractor member 541. For example, plunger member 584 may be configured to engage retractor member 541 in response to actuation by a user of button member 586 to reset retractor member 541 from a proximal position to a distal position, as will be explained in more detail below.

Button member 586 may be configured to be depressed by a user to advance plunger member 584 in a distal direction to engage and reset retractor member 541. After a user releases button member 586, spring member 588 may be configured to return button member 586 and plunger member 584 to their original position.

Plunger housing 582, plunger member 584, button member 586, and/or spring member 588 may be made out of any suitable materials as may serve a particular implementation. For example, plunger housing 582, plunger member 584, button member 586, and/or spring member 588 may be made out of stainless steel, titanium, a hard plastic, any other suitable material, and/or combinations thereof as may serve a particular implementation.

Figure 15:
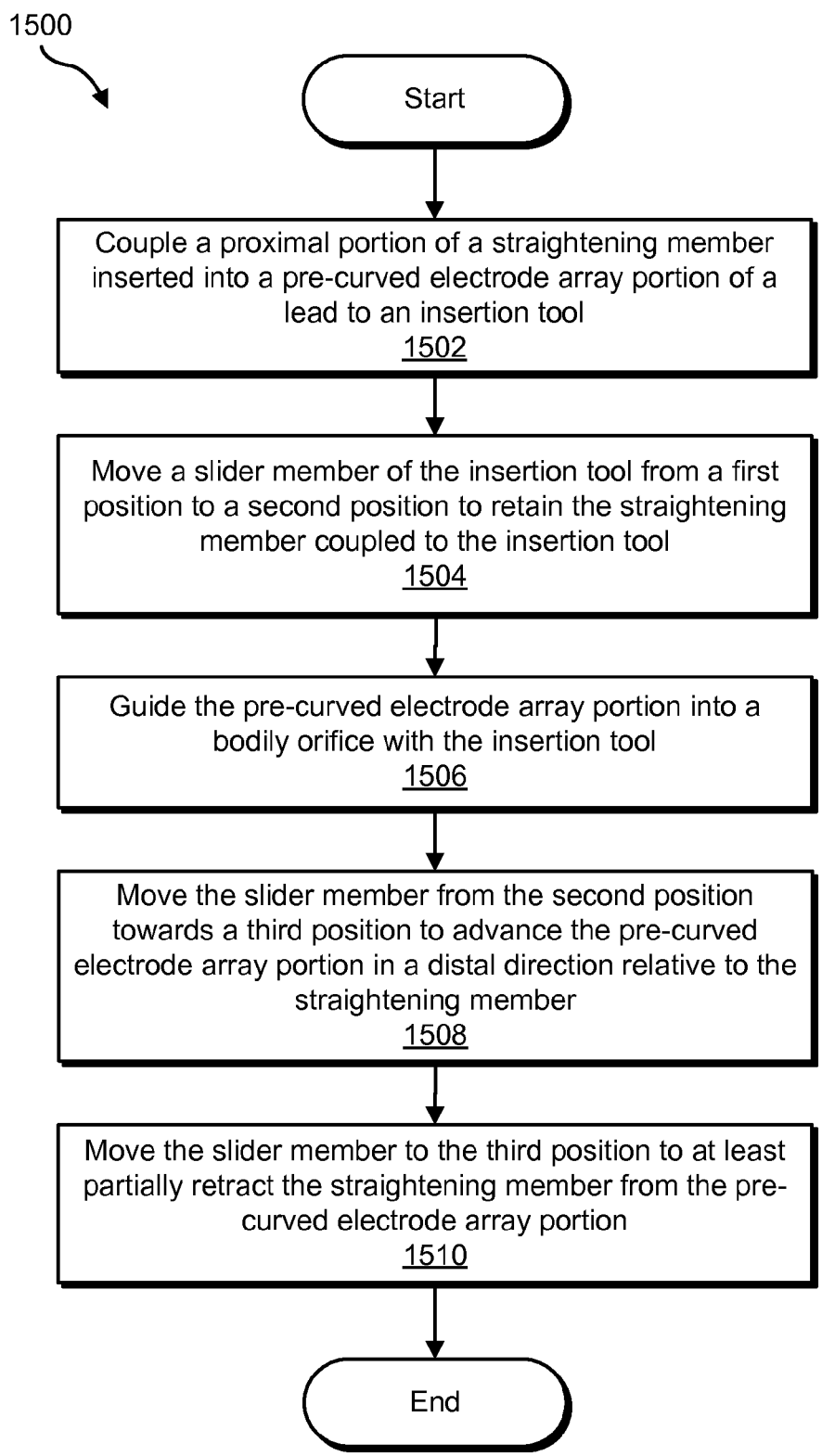
FIG. 15 illustrates an exemplary method of inserting a pre-curved electrode array portion of a lead into a bodily orifice according to principles described herein.

FIG. 15 illustrates an exemplary method 1500 of inserting a pre-curved electrode array portion of a lead into a bodily orifice. While FIG. 15 illustrates exemplary steps according to one embodiment, other embodiments may omit, add to, reorder, and/or modify any of the steps shown in FIG. 15.

In step 1502, a proximal portion of a straightening member inserted into a pre-curved electrode array portion of a lead may be coupled to an insertion tool. For example, FIG. 16A illustrates insertion tool 500 being coupled to straightening member 300, which is inserted into pre-curved electrode array portion 112 of lead 118 with the electrodes 114 facing as shown. As shown in FIG. 16A, to facilitate coupling of straightening member 300 to insertion tool 500, slider member 522 may be in a first position. The first position of slider member 522 is shown in greater detail in FIG. 16B, which illustrates a partial cross-sectional side view of insertion tool 500. As shown, slider member 522 may engage first detent 572 of detent plate 570 when slider member 522 is in the first position.

Figure 16C:
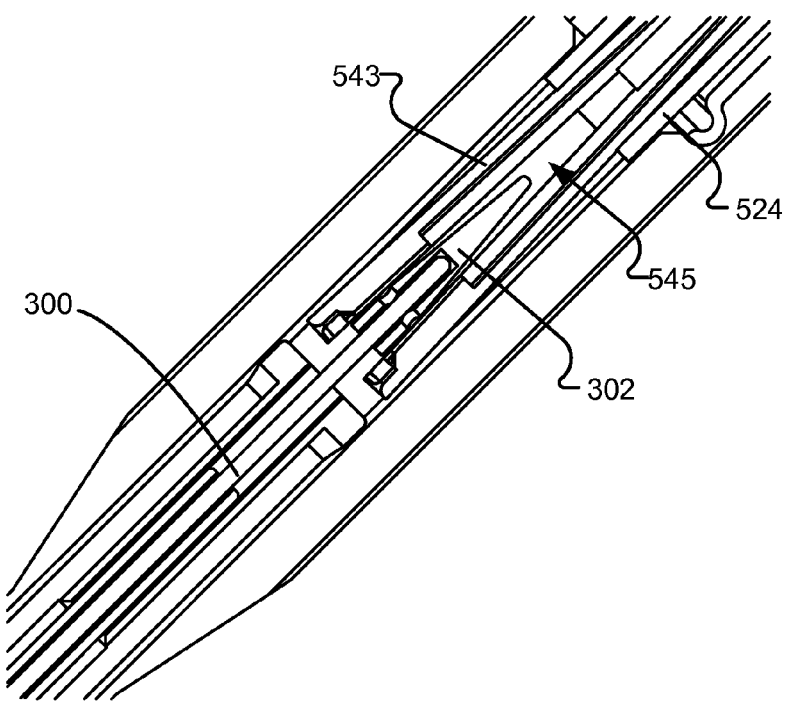
FIG. 16C shows an exemplary collet member expanding to receive a proximal portion of the straightening member of FIG. 16A according to principles described herein.
Figure 16D:
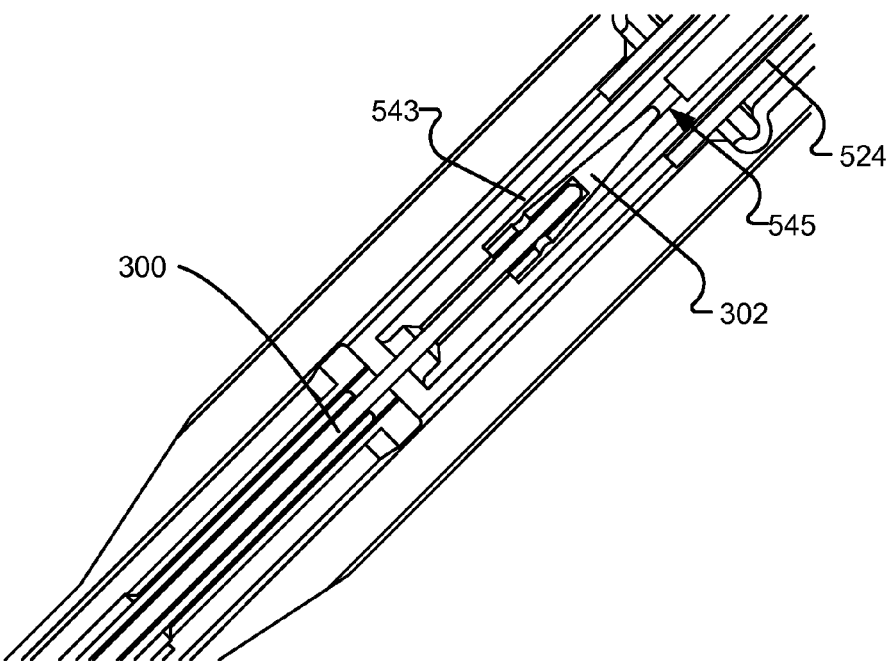
FIG. 16D shows the exemplary collet member of FIG. 16C returned to its unexpanded position with the proximal portion of the straightening member disposed therein according to principles described herein.

As shown in FIG. 16C, which illustrates a cross-sectional side view of proximal portion 302 of straightening member 300 being inserted into collet member 543, when slider member 522 is in the first position, a distal end of pusher tube 524 may be positioned proximal to at least a portion of collet member 543. This configuration may allow collet member 543 to expand to receive proximal portion 302 of straightening member 300. Once proximal portion 302 of straightening member 300 is fully inserted into lumen 545 of collet member 543, collet member 543 may return to its unexpanded position to retain proximal portion 302 within lumen 545, as shown in FIG. 16D.

Figure 16E:
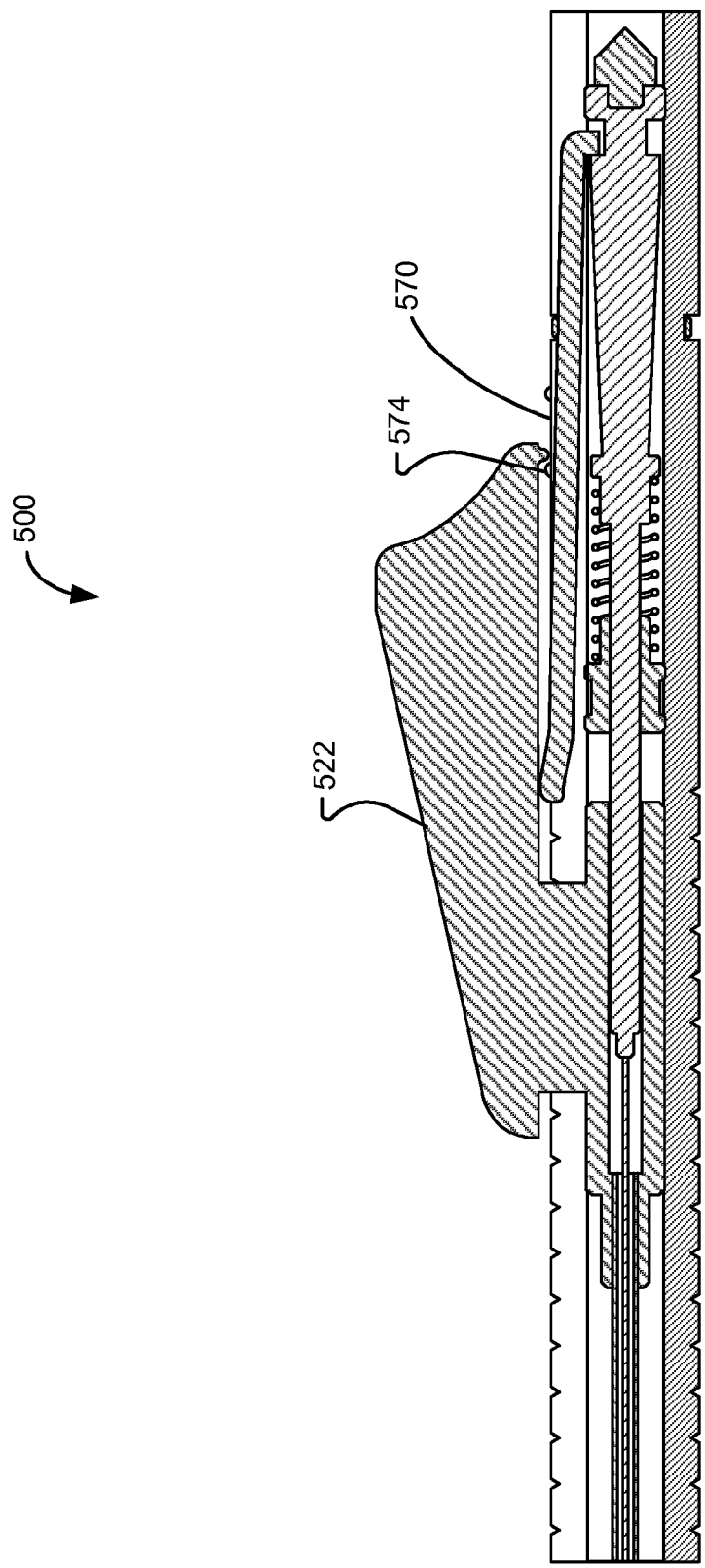
FIG. 16E shows the exemplary insertion tool of FIG. 16A with the exemplary slider member in a second position according to principles described herein.
Figure 16F:
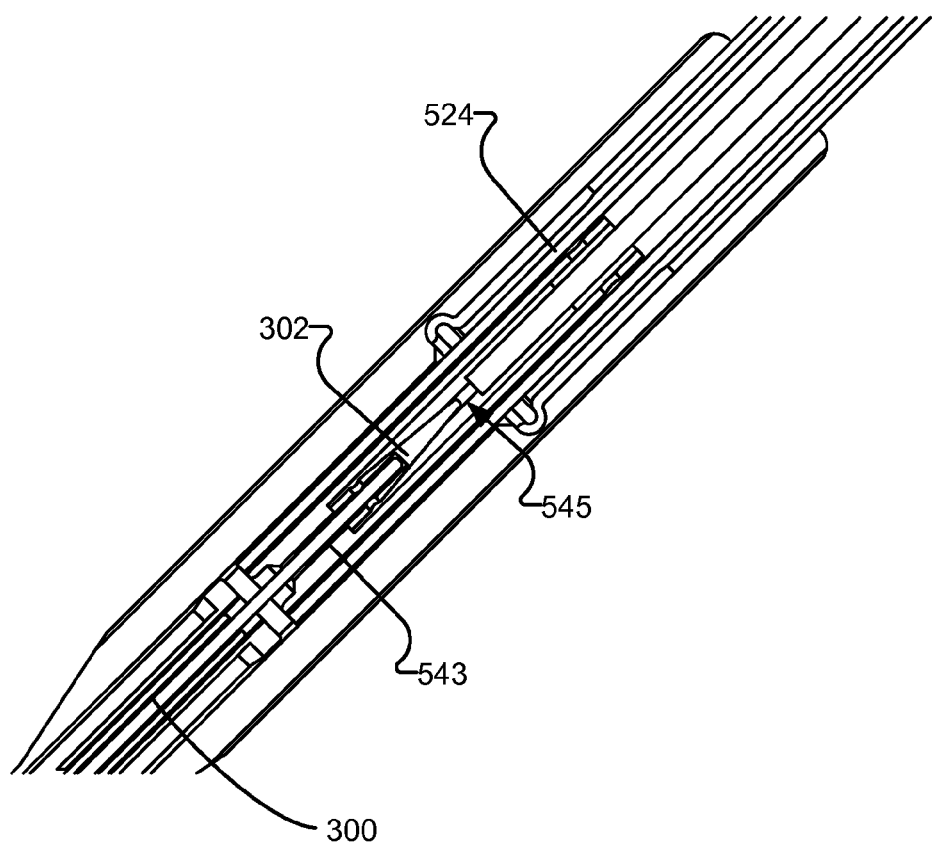
FIG. 16F shows an exemplary pusher tube covering the exemplary collet member according to principles described herein.

Returning to FIG. 15, in step 1504, a slider member of the insertion tool may be moved from a first position to a second position to retain the straightening member coupled to the insertion tool. For example, FIG. 16E shows a partial cross-sectional side view of insertion tool 500 with slider member 522 in the second position. As shown, when in the second position, slider member 522 may engage second detent 574 of detent plate 570. In some examples, moving slider member 522 from the first position to the second position may advance pusher tube 524 until a portion of pusher tube 524 covers collet member 543, as shown in FIG. 16F. In this manner, pusher tube 524 may resist further expansion of collet member 543 and thereby prevent proximal portion 302 of straightening member 300 from being removed from collet member 543.

Returning to FIG. 15, in step 1506, the pre-curved electrode array portion of the lead may be guided into a bodily orifice with the insertion tool. For example, a user (e.g., a surgeon) may advance pre-curved electrode array portion 112 into a bodily orifice using insertion tool 500. In some examples, the user may utilize insertion tool 500 to advance the pre-curved electrode array portion at least partially into one of the three parallel ducts of a human cochlea through a surgical opening in the cochlea wall.

Figure 16G:
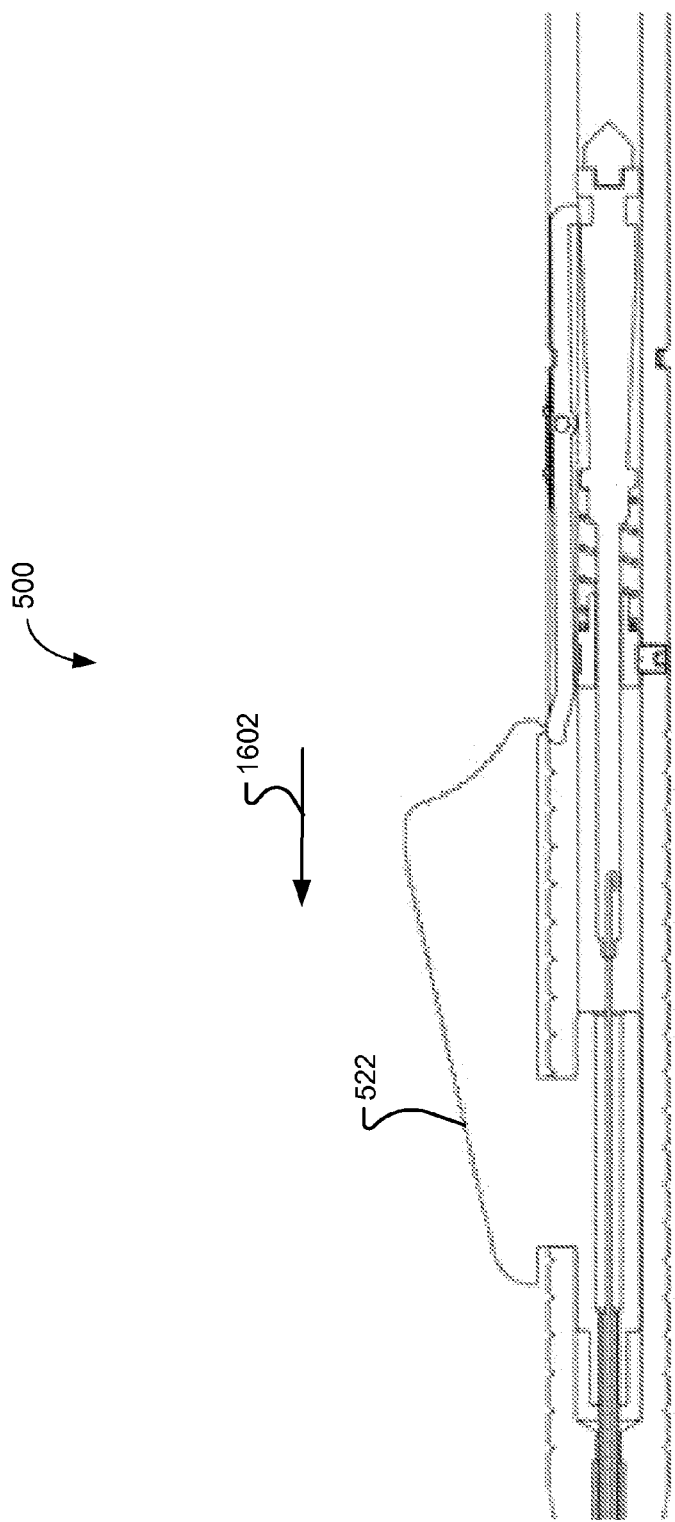
FIG. 16G shows the exemplary insertion tool of FIG. 16A with the exemplary slider member moving towards a third position according to principles described herein.
Figure 16H:
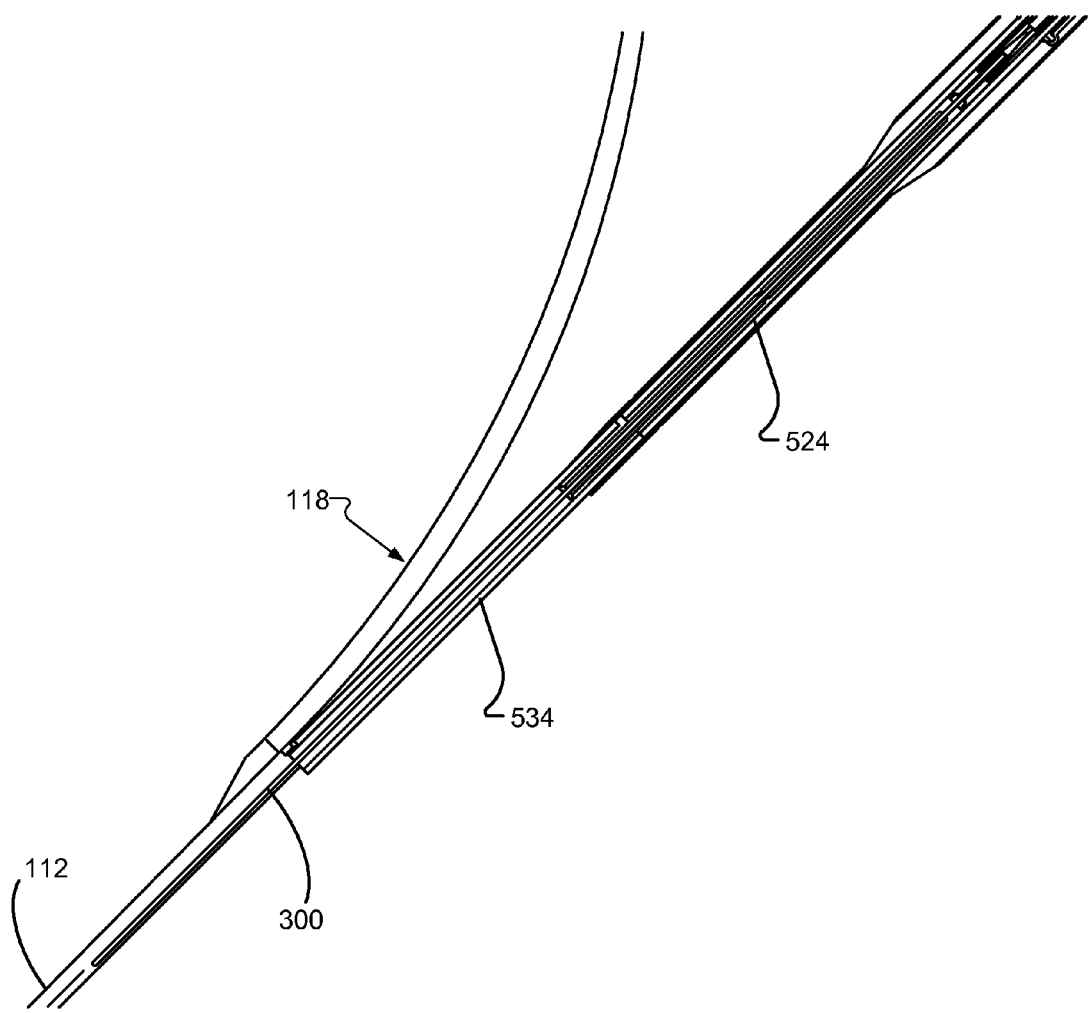
FIG. 16H shows an exemplary ejection member advancing a pre-curved electrode array portion of a lead in a distal direction relative to a straightening member according to principles described herein.

In step 1508, the slider member may be moved from the second position towards a third position to advance the pre-curved electrode array portion of the lead in a distal direction relative to the straightening member. For example, as shown in FIG. 16G, which illustrates a partial cross-sectional side view of insertion tool 500, slider member 522 may be advanced from the second position in a distal direction towards the third position as indicated by arrow 1602. As shown in FIG. 16H, as slider member 522 is moved from the second position towards the third position, pusher tube 524 may engage and advance ejection member 534 in a distal direction relative to holder member 532. As a result, ejection member 534 may push coupling portion 210 to advance lead 118 in a distal direction relative to straightening member 300, thereby pushing or advancing pre-curved electrode array portion 112 in a distal direction and at least partially off of straightening member 300. Additionally or alternatively, a proximal end of ejection member 534 may be coupled to a distal end of pusher tube 524.

In certain examples, ejection member 534 may be configured to advance the pre-curved electrode array portion 112 further into a cochlea. Additionally or alternatively, as pre-curved electrode array portion 112 is advanced off of straightening member 300, pre-curved electrode array portion 112 may move from a straightened configuration to a curved configuration to conform to the curvature of the cochlea.

Figure 16I:
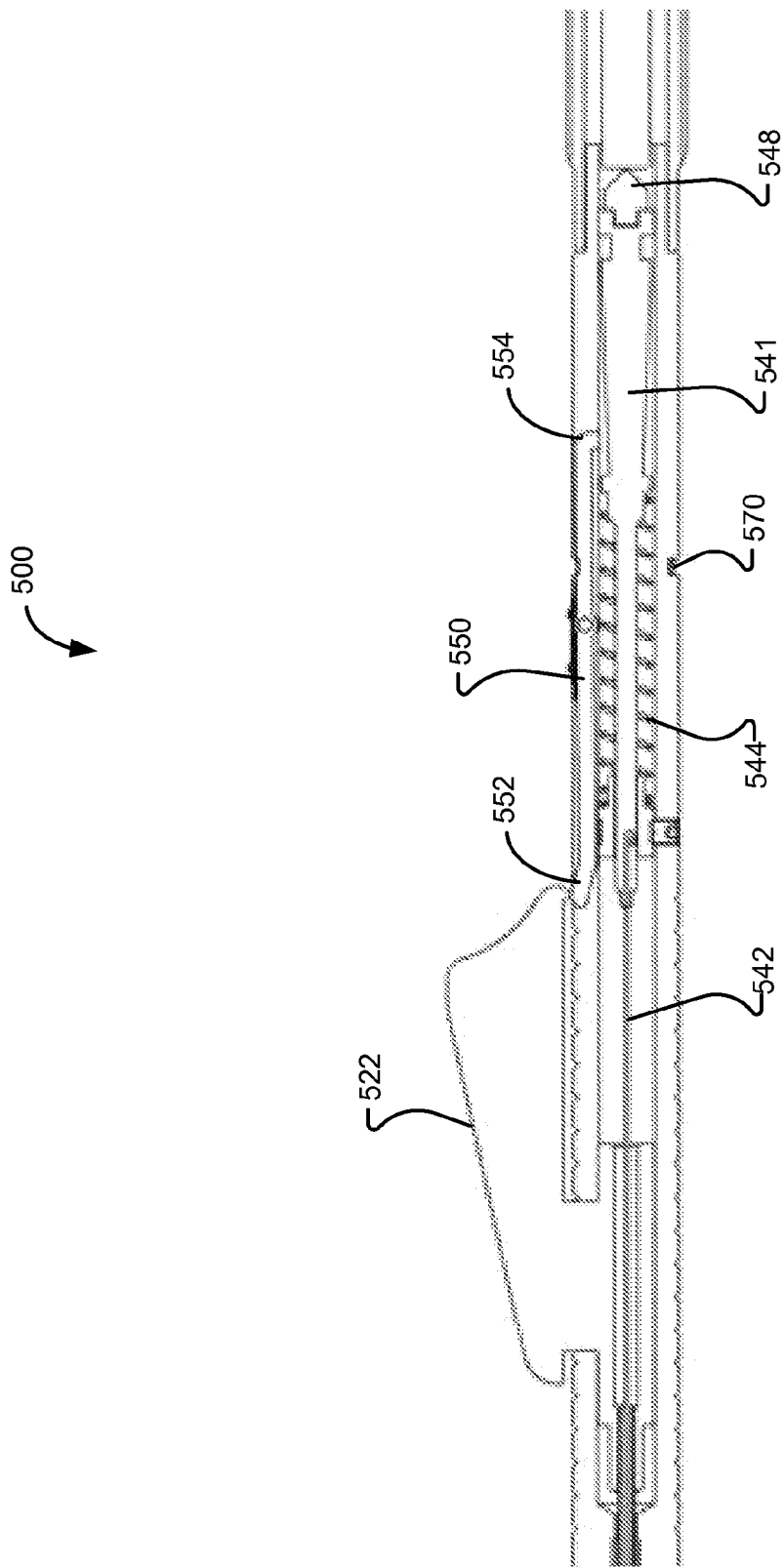
FIG. 16I shows the exemplary insertion tool of FIG. 16A with the exemplary slider member in a third position and engaging a distal end of an exemplary rocker lever to allow an exemplary retractor member to move from a distal position to a proximal position according to principles described herein.
Figure 16J:
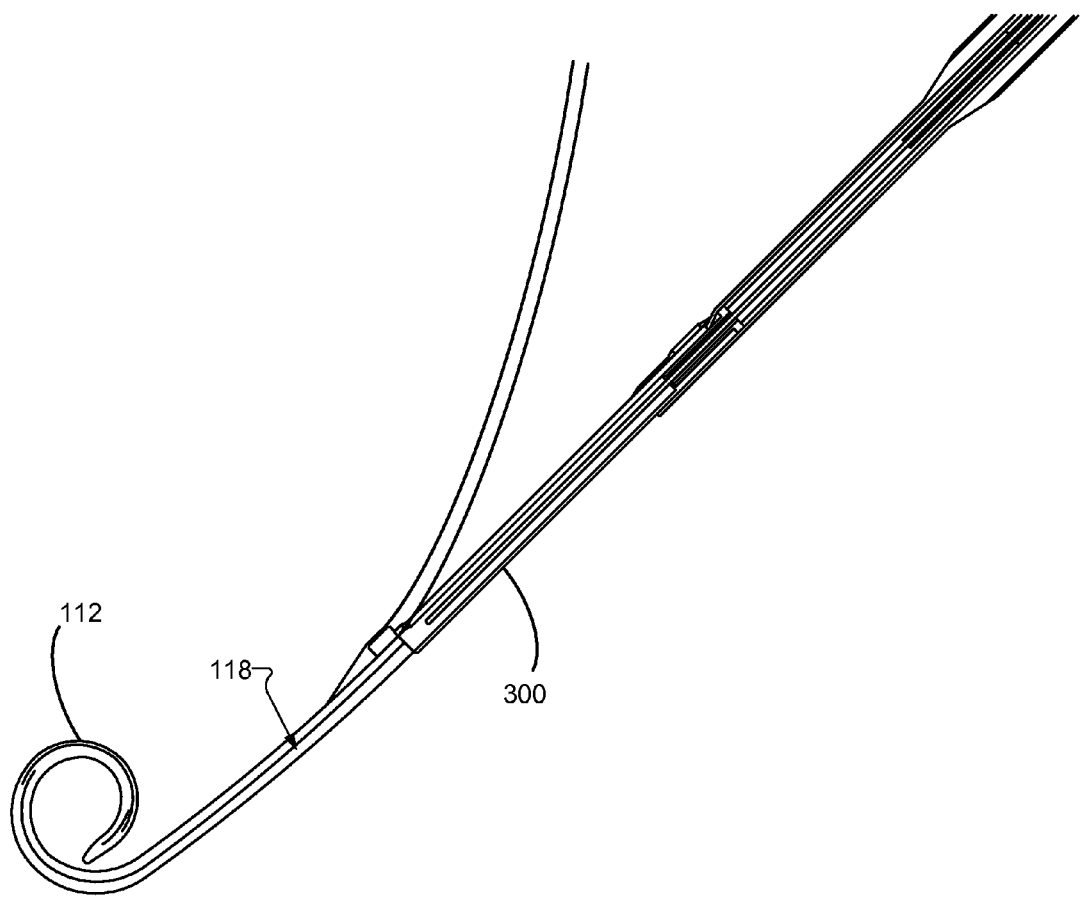
FIG. 16J shows an exemplary straightening member at least partially retracted from a pre-curved electrode array portion of a lead according to principles described herein.

Returning to FIG. 15, in step 1510, the slider member may be moved to the third position to at least partially retract the straightening member from the pre-curved electrode array portion. For example, FIG. 16I illustrates a cross-sectional side view of a portion of insertion tool 500 with slider member 522 in the third position. As shown, while in the third position, slider member 522 may engage distal portion 552 of rocker lever 550 to at least partially rotate rocker lever 550. As a result, proximal portion 554 may disengage retractor member 541 thereby allowing retractor member 541 to move (e.g., by the force of spring member 544) from a distal position (e.g., shown in FIG. 16G) to a proximal position (e.g., shown in FIG. 16I). Because collet member 543 is coupled to straightening member 300 and to retractor member 541 (e.g., by way of retractor wire 542), the movement of retractor member 541 to the proximal position may at least partially retract straightening member 300 from pre-curved electrode array portion 112 of lead 118, as shown in FIG. 16J. Once straightening member 300 has been retracted out of pre-curved electrode array portion 112, a user may withdraw insertion tool 500 away from pre-curved electrode array portion 112, leaving pre-curved electrode array portion 112 inserted within a human cochlea.

Figure 16K:
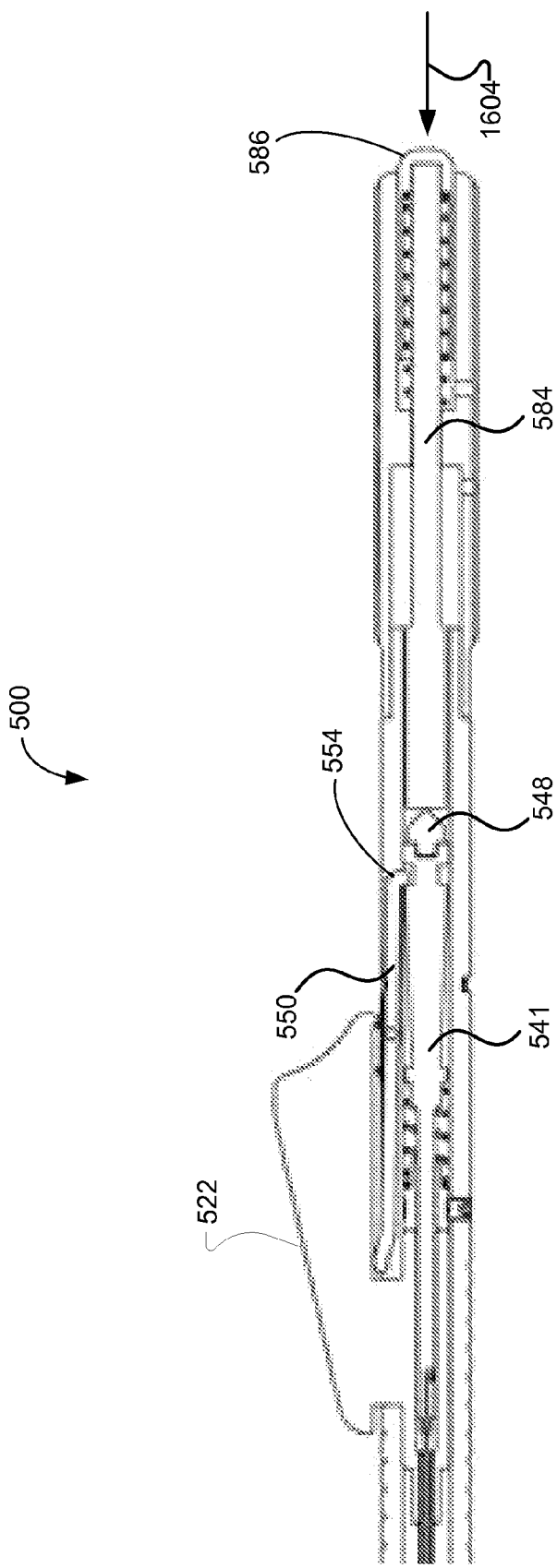
FIG. 16K shows the exemplary insertion tool of FIG. 16A with the exemplary slider member in the first position and an exemplary plunger assembly being actuated to reset the exemplary retractor assembly according to principles described herein.

Additionally or alternatively the user may reset retractor member 541 from the proximal position to the distal position, as shown in FIG. 16K. As shown, to reset retractor member 541, a user may return slider member 522 from the third position to the first position and then depress button member 586 to advance plunger member 584 in a distal direction, as indicated by arrow 1604. As a result, plunger member 584 may engage shock absorber 548 to advance retractor member 541 from the proximal position to the distal position. Once in the distal position, proximal portion 554 of rocker lever 550 may engage retractor member 541 to retain retractor member 541 in the distal position, thereby allowing insertion tool 500 to be re-used to insert a pre-curved electrode array portion of another lead into a bodily orifice.

The insertion tools described herein (e.g., insertion tool 500) may be configured to facilitate single-handed insertion of a lead into a bodily orifice. For example, a user may grasp handle portion 511 of insertion tool 500 with a single hand and guide pre-curved electrode array portion 112 into the cochlear duct. Once pre-curved electrode array portion 112 has been suitably positioned, the user may advance pre-curved electrode array portion 112 off of straightening member with the same hand by actuating slider member 522 with the thumb or forefinger. This actuation may be performed without substantially repositioning insertion tool 500 within the user's hand. In this manner, insertion tool 500 may provide a stable platform for the insertion of pre-curved electrode array portion 112 and minimize trauma to the cochlea that may occur during the insertion procedure.

A system of the present disclosure may include an insertion tool (e.g., insertion tool 500), a lead (e.g., lead 118), and a straightening member (e.g., straightening member 300) packaged together in the same sterile package for the convenience of the user. In some examples, straightening member 300 may be inserted into lead 118 but not coupled to insertion tool 500 before being packaged. Accordingly, the user (e.g., the surgeon) may have the option to either couple straightening member 300 to insertion tool 500 to insert lead 118 using insertion tool 500 or use a free hand method of inserting lead 118 with straightening member 300 without the use of insertion tool 500.

In some examples, insertion tool 500 and/or any component thereof may be disposable. For example, insertion tool 500 may be used during a single lead insertion procedure (or during two lead insertion procedures for a bilateral cochlear implant patient) and then disposed of. In this manner, insertion tool 500 does not need to be sterilized after use. Alternatively, insertion tool 500 may be sterilized after use so that it may be used in one or more subsequent lead insertion procedures.

Insertion tool 500 is provided for exemplary purposes only. One will appreciate that additional insertion tools according to principles described herein may include additional elements or may exclude certain elements.

The preceding description has been presented only to illustrate and describe embodiments of the invention. It is not intended to be exhaustive or to limit the invention to any precise form disclosed. Many modifications and variations are possible in light of the above teaching.

What is claimed is:

1. An insertion tool that facilitates insertion of a pre-curved electrode array portion of a lead into a bodily orifice, the insertion tool comprising:

a handle assembly that facilitates handling of the insertion tool;

a slider assembly disposed at least partially within the handle assembly and comprising
 a slider member configured to be actuated by a user to operate the insertion tool, and
 a pusher tube coupled to a distal end of the slider member and that advances in a distal direction relative to the handle assembly in response to an advancement by the user of the slider member in the distal direction relative to the handle assembly;

an insertion assembly coupled to the handle assembly and comprising a holder member configured to removably couple to the lead; and a retractor assembly disposed at least partially within the handle assembly and that selectively couples to a straightening member inserted into the pre-curved electrode array portion, the retractor assembly comprising a spring-loaded retractor member that moves from a distal position to a proximal position relative to the handle assembly in response to the advancement by the user of the slider member in the distal direction relative to the handle assembly to at least partially retract the straightening member from the pre-curved electrode array portion.

2. The insertion tool of claim 1, further comprising a rocker lever that selectively retains the spring-loaded retractor member in the distal position and releases the spring-loaded retractor member to move from the distal position to the proximal position in response to the advancement by the user of the slider member in the distal direction relative to the handle assembly.

3. The insertion tool of claim 2, wherein the retractor assembly further comprises:
a retractor wire coupled to a distal end of the spring-loaded retractor member and extending at least partially through the slider assembly; and
a collet member coupled to a distal end of the retractor wire and expandable to receive a proximal portion of the straightening member.

4. The insertion tool of claim 3, wherein the collet member is generally tubular and comprises one or more slits extending from a distal end thereof and configured to allow the collet member to expand, the collet member further comprising an internal ledge configured to resist removal of the proximal portion of the straightening member after the proximal portion of the straightening member is received into to collet member.

5. The insertion tool of claim 4, wherein the slider member is slidable relative to the handle assembly between a first position, a second position, and a third position, and wherein when the slider member is in the first position a distal end of the pusher tube is positioned proximal of the collet member to allow the collet member to expand, wherein when the slider member is in the second position a distal portion of the pusher tube covers the collet member to prevent the collet member from expanding, and wherein when the slider member is in the third position the slider member engages a distal end of the rocker lever to release the spring-loaded retractor member.

6. The insertion tool of claim 5, further comprising a detent plate coupled to the handle assembly and defining a first detent configured to provide tactile feedback to the user when the slider member is in the first position and a second detent configured to provide tactile feedback to the user when the slider member is in the second position, and wherein the slider member is configured to engage the first detent when the slider member is in the first position, to engage the second detent when the slider member is in the second position, and to engage the distal end of the rocker lever when the slider member is in the third position.

7. The insertion tool of claim 6, wherein the insertion assembly further comprises an ejection member disposed at least partially within and slidable relative to the holder member, and wherein the holder member comprises a slot in a distal end of the holder member configured to hold a portion of the lead.

8. The insertion tool of claim 7, wherein as the slider member moves from the second position to the third position, the pusher tube engages and advances the ejection member in a distal direction relative to the holder member to push and advance the lead off of the holder member and the pre-curved electrode array portion at least partially off of the straightening member.

9. The insertion tool of claim 8, wherein the ejection member comprises a slot extending along a length thereof and wherein the holder member comprises a tab extending at least partially into the slot of the ejection member to limit relative movement between the holder member and the ejection member.

10. The insertion tool of claim 9, wherein the handle assembly comprises a handle portion configured to at least partially contain the retractor assembly and the slider assembly and a guide tube coupled to a distal end of the handle portion, wherein the handle portion comprises a lumen in communication with a lumen of the guide tube, and wherein the pusher tube of the slider assembly is disposed at least partially through and slidable relative to the guide tube.

11. The insertion tool of claim 10, wherein the guide tube is configured to selectively couple to the holder member.

12. The insertion tool of claim 11, wherein the holder member is configured to be rotatable relative to the guide tube to facilitate selective insertion of the pre-curved electrode array portion in a right cochlea or a left cochlea.

13. The insertion tool of claim 10, wherein the guide tube extends away from the handle portion at a predefined angle.

14. The insertion tool of claim 10, further comprising a plunger assembly configured to reset the spring-loaded retractor member from the proximal position to the distal position, wherein the plunger assembly comprises:
a plunger housing coupled to a proximal end of the handle portion and defining a lumen extending therethrough in communication with the lumen of the handle portion;
a plunger member disposed at least partially within the lumen of the plunger housing and slidable relative to the plunger housing and handle portion; and
a button member coupled to the plunger member and extending from a proximal end of the plunger housing, wherein the button member is configured to be actuated by the user to move the plunger member in a distal direction to engage the spring-loaded retractor member and return the spring-loaded retractor member from the proximal position to the distal position.

15. The insertion tool of claim 14, further comprising a radial spring configured to engage the rocker lever and exert a rotational force on the rocker lever opposite a rotational force exerted on the rocker lever by actuation of the slider member.

16. The insertion tool of claim 1, further comprising an air dampening mechanism configured to dampen movement of the spring-loaded retractor member.

17. The insertion tool of claim 1, wherein the slider assembly comprises a single piece of molded plastic.

18. A system comprising:
a lead comprising a pre-curved electrode array portion and configured to be coupled to an implantable cochlear stimulator;
a straightening member inserted into the pre-curved electrode array portion to retain the pre-curved electrode array portion in a straightened configuration; and
an insertion tool that facilitates insertion of the pre-curved electrode array portion into a cochlea of a patient the insertion tool comprising:
a handle assembly that facilitates handling of the insertion tool;
a slider assembly disposed at least partially within the handle assembly and comprising a slider member configured to be actuated by a user to operate the insertion tool, and a pusher tube coupled to a distal end of the slider member and that advances in a distal direction relative to the handle assembly in response to an advancement by the user of the slider member in the distal direction relative to the handle assembly;

an insertion assembly coupled to the handle assembly and comprising a holder member configured to removably couple to the lead; and a retractor assembly disposed at least partially within the handle assembly and that selectively couples to the straightening member inserted into the pre-curved electrode array portion, the retractor assembly comprising a spring-loaded retractor member that moves from a distal position to a proximal position relative to the handle assembly in response to the advancement by the user of the slider member in the distal direction relative to the handle assembly to at least partially retract the straightening member from the pre-curved electrode array portion.

19. The system of claim 18, wherein the insertion tool further comprises a rocker lever that selectively retains the spring-loaded retractor member in the distal position and releases the spring-loaded retractor member to move from the distal position to the proximal position in response to the advancement by the user of the slider member in the distal direction relative to the handle assembly.

20. The system of claim 19, wherein the retractor assembly further comprises:

a retractor wire coupled to a distal end of the spring-loaded retractor member; and a collet member coupled to a distal end of the retractor wire and expandable to receive a proximal portion of the straightening member, wherein the collet member is generally tubular and comprises one or more slits extending from a distal end thereof and configured to allow the collet member to expand, the collet member further comprising an internal ledge configured to resist removal of the proximal portion of the straightening member after the proximal portion of the straightening member is received into to collet member.

21. The system of claim 20, wherein the slider member is slidable relative to the handle assembly between a first position, a second position, and a third position, and wherein when the slider member is in the first position a distal end of the pusher tube is positioned proximal of the collet member to allow the collet member to expand, wherein when the slider member is in the second position a distal portion of the pusher tube covers the collet member to prevent the collet member from expanding, and wherein when the slider member is in the third position the slider member engages a distal end of the rocker lever to release the spring-loaded retractor member.

22. A method of inserting a pro-curved electrode array portion of a lead into a bodily orifice, the method comprising:

coupling a proximal portion of a straightening member inserted into the pre-curved electrode array portion to an insertion tool, the insertion tool comprising a handle assembly that facilitates handling of the insertion tool, a slider assembly disposed at least partially within the handle assembly and comprising a slider member configured to be actuated by a user to operate the insertion tool, and a pusher tube coupled to a distal end of the slider member and that advances in a distal direction relative to the handle assembly in response to an advancement by the user of the slider member in the distal direction relative to the handle assembly, an insertion assembly coupled to the handle assembly and comprising a holder member configured to removably couple to the lead, and a retractor assembly disposed at least partially within the handle assembly and that selectively couples to the straightening member inserted into the pre-curved electrode array portion, the retractor assembly comprising a spring-loaded retractor member that moves from a distal position to a proximal position relative to the handle assembly in response to the advancement by the user of the slider member in the distal direction relative to the handle assembly to at least partially retract the straightening member from the pre-curved electrode array portion;

moving the slider member in the distal direction relative to the handle assembly from a first position to a second position to retain the straightening member coupled to the retractor assembly;

guiding the pre-curved electrode array portion into a bodily orifice with the insertion tool;

moving the slider member in the distal direction relative to the handle assembly from the second position towards a third position to advance the pre-curved electrode array portion in a distal direction relative to the straightening member; and moving the slider member in the distal direction relative to the handle assembly to the third position to release the spring-loaded retractor member to move from the distal position to the proximal position to at least partially retract the straightening member from the pre-curved electrode array portion.

23. The method of claim 22, wherein the insertion tool further comprises a plunger assembly configured to reset the spring-loaded retractor member from the proximal position to the distal position, and wherein the method further comprises actuating the plunger assembly to reset the spring-loaded retractor member to the distal position.

* * * * *